US012780921B2

(12) United States Patent
Stauton et al.

(10) Patent No.: US 12,780,921 B2
(45) Date of Patent: Nov. 3, 2026

(54) COMPOSITION OF TRIAX ANTIBODIES AND METHOD OF MAKING AND USING THEREOF

(71) Applicant: ARBELE LIMITED, Hong Kong (CN)

(72) Inventors: Donald E. Stauton, Kirkland, WA (US); John Moonching Luk, Bellevue, WA (US)

(73) Assignee: ARBELE Corporation, Bellevue, WA (US)

( * ) Notice: Subject to any disclaimer, the term of this patent is extended or adjusted under 35 U.S.C. 154(b) by 1112 days.

(21) Appl. No.: 17/778,407

(22) PCT Filed: Dec. 4, 2020

(86) PCT No.: PCT/US2020/063461
§ 371 (c)(1),
(2) Date: May 19, 2022

(87) PCT Pub. No.: WO2021/113748
PCT Pub. Date: Jun. 10, 2021

(65) Prior Publication Data

US 2023/0340119 A1 Oct. 26, 2023

Related U.S. Application Data

(60) Provisional application No. 62/944,230, filed on Dec. 5, 2019.

(51) Int. Cl.

| | |
|---|---|
| ***C07K 16/28*** | (2006.01) |
| ***A61K 39/395*** | (2006.01) |
| ***A61K 45/06*** | (2006.01) |
| ***A61P 35/04*** | (2006.01) |
| ***C07K 16/30*** | (2006.01) |
| ***C07K 16/40*** | (2006.01) |

(52) U.S. Cl.
CPC ...... *C07K 16/2809* (2013.01); *A61K 39/3955* (2013.01); *A61K 39/39558* (2013.01); *A61K 45/06* (2013.01); *A61P 35/04* (2018.01); *C07K 16/2845* (2013.01); *C07K 16/2896* (2013.01); *C07K 16/30* (2013.01); *C07K 16/40* (2013.01); *C07K 2317/31* (2013.01); *C07K 2317/35* (2013.01); *C07K 2317/524* (2013.01); *C07K 2317/526* (2013.01); *C07K 2317/53* (2013.01); *C07K 2317/622* (2013.01); *C07K 2317/73* (2013.01); *C07K 2317/76* (2013.01); *C07K 2317/92* (2013.01)

(58) Field of Classification Search
CPC ............ C07K 16/2809; C07K 16/2878; C07K 16/2896; C07K 16/30; C07K 16/40; C07K 2317/31; C07K 2317/24; C07K 2317/2878; C07K 2317/524; C07K 2317/526; C07K 2317/53; C07K 2317/565; C07K 2317/622; C07K 2317/73; C07K 2317/76; C07K 2317/92; A61K 39/3955; A61K 39/39558
See application file for complete search history.

(56) References Cited

U.S. PATENT DOCUMENTS

| | | | | |
|---|---|---|---|---|
| 2009/0155256 | A1 | 6/2009 | Black et al. | |
| 2009/0155275 | A1* | 6/2009 | Wu | A61P 35/02 530/387.3 |
| 2010/0256340 | A1 | 10/2010 | Brinkmann et al. | |
| 2013/0078250 | A1 | 3/2013 | Ast et al. | |
| 2014/0120581 | A1* | 5/2014 | Niwa | C07K 16/468 435/69.6 |
| 2014/0294823 | A1 | 10/2014 | Moore et al. | |
| 2015/0307628 | A1 | 10/2015 | Kim et al. | |
| 2017/0129961 | A1 | 5/2017 | Raum et al. | |
| 2017/0198052 | A1 | 7/2017 | Lin et al. | |
| 2017/0218078 | A1 | 8/2017 | Raum et al. | |
| 2018/0022807 | A1 | 1/2018 | Kasturirangan et al. | |
| 2018/0094059 | A1 | 4/2018 | Sahin et al. | |
| 2018/0142021 | A1 | 5/2018 | Weiss et al. | |
| 2019/0016801 | A1 | 1/2019 | Hofmann et al. | |
| 2019/0046655 | A1 | 2/2019 | Staunton | |
| 2019/0127481 | A1 | 5/2019 | Plückthun et al. | |

FOREIGN PATENT DOCUMENTS

WO WO 2019/222428 A 11/2019

OTHER PUBLICATIONS

Paul, Fundamental Immunology, 3rd Edition, pp. 292-295. (Year: 1993).*
Murphy et al., Journal of Immunological Methods, vol. 463, p. 127-133. (Year: 2018).*

* cited by examiner

*Primary Examiner* — Hong Sang
(74) *Attorney, Agent, or Firm* — EpiMED LLC

(57) ABSTRACT

A multi-specific antibody having a N-terminus and a C-terminus, comprising a first monomer, comprising from the N-terminus to the C-terminus, a VL domain, first linker, and a first Fc domain, a second monomer, comprising from the N-terminus to the C-terminus, a VH domain, a second linker, and a second Fc domain, and at least a first binding domain linked to either the N-terminus or the C-terminus of the multi-specific antibody, wherein the first monomer and the second monomer are paired through the interaction between the VL domain and the VH domain, and wherein the multi-specific antibody is stabilized by a disulfide bond between the first linker and the second linker.

17 Claims, 15 Drawing Sheets

Specification includes a Sequence Listing.

DIQMTQSPSSLSASVGDRVTITCQASQDISNYLNWYQQKPGKAPKLLIYYTSRLESGVPSRF
SGSGSGTDYTLTISSLQPEDFATYYCQQGNTLPWTFGQGTKVEIK (SEQ ID 13)

Germline CDR-L1 : RASQDIRNY (SEQ ID 17)
L4 substitutions: R24Q, R30S

Figure 7

| | Average Kd (nM) | Range Kd (nM) |
|---|---|---|
| WT | 60 | 50, 54, 75 |
| L4 | 320 | 236, 358, 365 |

COMPOSITION OF TRIAX ANTIBODIES AND METHOD OF MAKING AND USING THEREOF

CROSS REFERENCE TO RELATED APPLICATIONS

This application is a national stage application of international application number PCT/US2020/063461, filed Dec. 4, 2020, which claims the benefit of the filing date of U.S. Provisional Application Ser. No. 62/944,230 filed Dec. 5, 2019, under 35 U.S.C. 119 (e), the entire disclosures of which are incorporated by reference herein.

SEQUENCE LISTING

The content of the ASCII text file of the sequence listing named "ARTI906US-ST25", which is 86,000 bytes in size was created on May 19, 2026, is incorporated herein by reference in its entirety.

TECHNICAL FIELD

The present disclosure generally relates to the technical field of cancer immunotherapy, and more particularly to composition of modified antibodies with multiple antigen binding specificities.

BACKGROUND

Unless otherwise indicated herein, the materials described in this section are not prior art to the claims in this application and are not admitted to be prior art by inclusion in this section.

Despite the recent advances in drug discovery and clinical imaging, cancer remains one of the deadliest diseases in humans. Our understandings on how tumor initiates, survives under stress, colonizes/metastasizes to distant organs and sites, and becomes resistant to drugs are still limited. The American Cancer Society estimated new cases of cancer in the US in 2014 is 1.6 million, with no approved curative treatment for most of the predominant types of cancer.

Gastrointestinal (GI) cancers (colorectal, gastric, pancreatic, esophageal, bile duct and liver) are leading causes of morbidity and mortality worldwide. Colorectal carcinoma (CRC) alone represents approximately 10% of all cancer diagnosis and is the second leading cause of cancer deaths world-wide. In China, liver and stomach cancers are among the most lethal of malignancies worldwide and over half of the incidences diagnosed, causing >1.42 million deaths per year globally, which are believed attributable to the viral/bacterial endemic (Hepatitis B virus [HBV] and *Helicobacter pylori* infections), chemical intoxications, environmental pollutions and food contaminations. There are no effective therapies. New biomarkers and therapeutic targets are thus needed for potential drug development against these aggressive cancers. A proven molecular targeting agent that can eliminate or repress the growth of these cancers will have important clinical value and significant market impact. These tumors can be resected effectively by surgery if the diseases are diagnosed in early stages. Unfortunately, and very often, most of GI cancers are asymptomatic and detected at very advanced stages when presented in the clinic. Without effective treatment, these patients die shortly after the diagnosis or relapse after salvage therapies.

CDH17 is a prominent cancer biomarker characterized by its overexpression in both liver and stomach cancers but not normal tissues from healthy adults. Anti-CDH17 monoclonal antibody displays the growth inhibitory effect on liver and stomach tumour cells. CDH17 is highly expressed in metastatic cancers, and the blockage of CDH17 expression and functions can markedly reduce lung metastasis of hepatocellular carcinoma (HCC). These observations indicate that humanized anti-CDH17 antibody may be developed as target therapeutics for treating cancer patients with indication of CDH17 biomarker in tumour tissues and/or in serum samples. While antibody drug conjugates are promising as an antibody therapy, multi-specific antibody therapeutics take advantage of immune responses to cancer and activate T cell-mediated cytotoxicity to cancer cells.

Bispecific antibodies that target CD3 positive T cells and CD19 positive B cells are proved to be effective for treating hematologic malignancies (Labrijn 2019, Yu 2017, Suurs 2019, and Bates 2019). However, attempts for targeting solid tumours show limited success, possibly due to lack of access to solid tumor cells and suitable immunomodulation signals. There is a need for an antibody-based scaffold for efficient targeting of multiple tumor antigens and immune cell antigens or products to generate more effective immunotherapeutics that better address the complexities of a pro-tumor microenvironment and mechanisms of tumor escape.

SUMMARY

In one aspect, the application provides multi-specific antibodies. The antibody may be bi-specific, tri-specific, tetra-specific or penta-specific. The antibody may have truncated structure.

In one embodiment, the application provides a multi-specific antibody having a N-terminus and a C-terminus, comprising a first monomer, comprising from the N-terminus to the C-terminus, a VL domain, first linker, and a first Fc domain, a second monomer, comprising from the N-terminus to the C-terminus, a VH domain, a second linker, and a second Fc domain, and at least a first binding domain linked to either the N-terminus or the C-terminus of the multi-specific antibody, wherein the first monomer and the second monomer are paired through the interaction between the VL domain and the VH domain, and wherein the multi-specific antibody is stabilized by a disulfide bond between the first linker and the second linker.

In one embodiment, the first binding domain is linked to the VH domain at the N-terminus, the VL domain at the N-terminus, the first Fc domain at the C-terminus, or the second Fc domain at the C-terminus.

In one embodiment, the multi-specific antibody further includes a second binding domain, and the antibody is tri-specific. In one embodiment, first binding domain is linked to the C-terminus of the first Fc domain and the second binding domain is linked to the C-terminus at the second Fc domain. In one embodiment, first binding domain is linked to the N-terminus at the VH domain and the second binding domain is linked to the C-terminus of the first Fc domain.

In one embodiment, the multi-specific antibody further includes a second binding domain, and the antibody is a tri-specific antibody. In one embodiment, the first binding domain and the second binding domain are linked to the opposite termini of the antibody. In one embodiment, the first binding domain and the second binding domain are linked to the same terminus of the antibody. In one embodiment, the first binding domain is linked to the N-terminus at the VH domain and the second binding domain is linked to the N-terminus at the VL domain.

In one embodiment, the multi-specific antibody further includes a third binding domain, and the antibody is a tetra-specific antibody. In one embodiment, the first binding domain is linked to the N-terminus at the VH domain, the second binding domain is linked to the N-terminus at the VL domain, and the third binding domain is linked to the C-terminus at the first Fc domain or the C-terminus at the second Fc domain.

In one embodiment, the multi-specific antibody above further includes a fourth binding domain, and the antibody is penta-specific. In one embodiment, the third binding domain is linked to the C-terminus at the first Fc domain and the fourth binding domain is linked to the C-terminus at the second Fc domain.

All the binding domains may have the binding affinity toward different antigens. Alternatively, certain binding domain may have the binding affinity toward the same antigen as another binding domain. In one embodiment, the first and the second binding are the same. In one embodiment, the first and the second binding are different. In one embodiment, the first, second and third binding domains are different from each other. In one embodiment, the first, second and third binding domains are different from each other and wherein the fourth binding domain is the same to one of the first, second and third binding domains.

Each first binding domain may be independently selected from a group consisting of a scFv domain, a ligand, a single domain nanobody, the binding region of a natural protein, a chemokine and a cytokine.

In one embodiment, the bi-specific antibody may have the first monomer comprising an amino acid sequence having at least 98% of sequence identity to SEQ ID NO: 1 and the second monomer comprising an amino acid sequence having at least 98% of sequence identity to SEQ ID NO: 2.

In one embodiment, the bi-specific antibody may have the first monomer comprising an amino acid sequence having at least 98% of sequence identity to SEQ ID NO: 1 and the second monomer comprising an amino acid sequence having at least 98% of sequence identity to SEQ ID NO: 3. In one embodiment, the bi-specific antibody may have the first monomer comprising an amino acid sequence having at least 98% of sequence identity to SEQ ID NO: 1 and the second monomer comprising an amino acid sequence having at least 98% of sequence identity to SEQ ID NO: 4. In one embodiment, the bi-specific antibody may have the first monomer comprising an amino acid sequence having at least 98% of sequence identity to SEQ ID NO: 5 and the second monomer comprising an amino acid sequence having at least 98% of sequence identity to SEQ ID NO: 6.

In one embodiment, the tri-specific antibody may have the first monomer comprising an amino acid sequence having at least 98% of sequence identity to SEQ ID NO: 7 and the second monomer c comprising an amino acid sequence having at least 98% of sequence identity to SEQ ID NO: 8. In one embodiment, the tri-specific antibody may have the first monomer comprising an amino acid sequence having at least 98% of sequence identity to SEQ ID NO: 9 and the second monomer comprising an amino acid sequence having at least 98% of sequence identity to SEQ ID NO: 10. In one embodiment, the tri-specific antibody may have the first monomer comprising an amino acid sequence having at least 98% of sequence identity to SEQ ID NO: 11 and the second monomer comprising an amino acid sequence having at least 98% of sequence identity to SEQ ID NO: 2. In one embodiment, the tri-specific antibody may have the first monomer comprising an amino acid sequence having at least 98% of sequence identity to SEQ ID NO: 12 and the second monomer comprising an amino acid sequence having at least 98% of sequence identity to SEQ ID NO: 4. In one embodiment, the tri-specific antibody may have the first monomer comprising an amino acid sequence having at least 98% of sequence identity to SEQ ID NO: 12 and the second monomer comprising an amino acid sequence having at least 98% of sequence identity to SEQ ID NO: 2.

20 In one embodiment, the tetra-specific antibody may have the first monomer comprising an amino acid sequence having at least 98% of sequence identity to SEQ ID NO: 14 and the second monomer comprising an amino acid sequence having at least 98% of sequence identity to SEQ ID NO: 15.

In one embodiment, the penta-specific antibody may have the first monomer comprising an amino acid sequence having at least 98% of sequence identity to SEQ ID NO: 14 and the second monomer comprising an amino acid sequence having at least 98% of sequence identity to SEQ ID NO: 16.

In one embodiment, the binding domains may be attached to the multi-specific antibody through a linker. In one embodiment, the linker comprises a proline-rich amino acid sequence. In one embodiment, the linker may include at least 20%, 30% or 50% of proline residue. In on embodiment, the linker may include from about 2 to about 31 amino acids.

In another aspect, the application provides isolated nucleic acid sequences encoding the multi-specific antibodies as disclosed thereof.

In a further aspect, the application provides expression vectors comprising the isolated nucleic acid sequences as disclosed thereof.

In a further aspect, the application provides a host cell comprising the isolated nucleic acid sequence as disclosed thereof.

In a further aspect, the application provides methods for producing the multi-specific antibodies as disclosed thereof. In one embodiment, the method includes the steps of culturing a host cell such that the DNA sequence encoding the multi-specific antibodies is expressed, and purifying said multi-specific antibody.

In a further aspect, the application provides methods of making the multi-specific antibodies. In one embodiment, the method includes the steps of culturing a host cell under conditions wherein said multi-specific antibodies is produced and recovering said antibody.

In a further aspect, the application provides immunoconjugates. In one embodiment, the immunoconjugate comprises the multi-specific antibody and a cytotoxic agent. In one embodiment, the immunoconjugate comprises the multi-specific antibody and an imaging agent.

In a further aspect, the application provides pharmaceutical compositions. In one embodiment, the pharmaceutical composition includes the multi-specific antibody and a pharmaceutically acceptable carrier. In one embodiment, the pharmaceutical composition may further include radioisotope, radionuclide, a toxin, a therapeutic agent, a chemotherapeutic agent or a combination thereof. In one embodiment, the pharmaceutical composition may include the immunoconjugate as disclosed above and a pharmaceutically acceptable carrier.

In a further aspect, the application provides methods for treating or preventing a cancer in a subject. In one embodiment, the method includes the step of administering to the subject a pharmaceutical composition comprising a purified multi-specific antibody as disclosed herein. In one embodiment, the method of treating a subject with a cancer includes the step of administering to the subject an effective amount of the multi-specific antibody as disclosed herein. In one embodiment, the method may further include co-administering an effective amount of a therapeutic agent. In one embodiment, the therapeutic agent comprises an antibody, a chemotherapy agent, an enzyme, or a combination thereof. The subject may be a human.

In a further aspect, the application provides a solution comprising an effective concentration of the multi-specific antibody as disclosed herein, wherein the solution is blood plasma in a subject.

BRIEF DESCRIPTION OF THE DRAWINGS

Embodiments according to the present disclosure may now be described with reference to the figures, in which like reference numerals denote like elements.

FIGS. 3A-3C, shows the production and binding specificities of TriAx-C;

FIGS. 5A-5F, shows the redirected T cell cytotoxicity by TriAx-A antibody targeting TROP2;

FIGS. 6A-6B, shows the redirected T cell cytotoxicity by TriAx-A antibody targeting FAP;

FIG. 7 depicts the amino acid sequences of the low affinity anti-CD3 binding domain (L4, SEQ ID NO: 13) and the germline CDR-L1 with the amino acid substitutions (SEQ ID NO: 17);

FIGS. 8A-8B, shows that TriAx-A harboring L4 displays reduced T cell affinity and activation;

FIGS. 9A-9B, shows that TriAx-A harboring L4 mediates cytotoxicity comparable to TriAx-A without L4 mutations;

FIGS. 11A-11D depicts the steric effect of additional binding domains to the function of TriAx core such as anti-CD3 binding affinity;

FIGS. 12A-12D depicts stabilized scFv (LocV) binding domains in TriAx antibodies.

DETAILED DESCRIPTION

Figure 1:
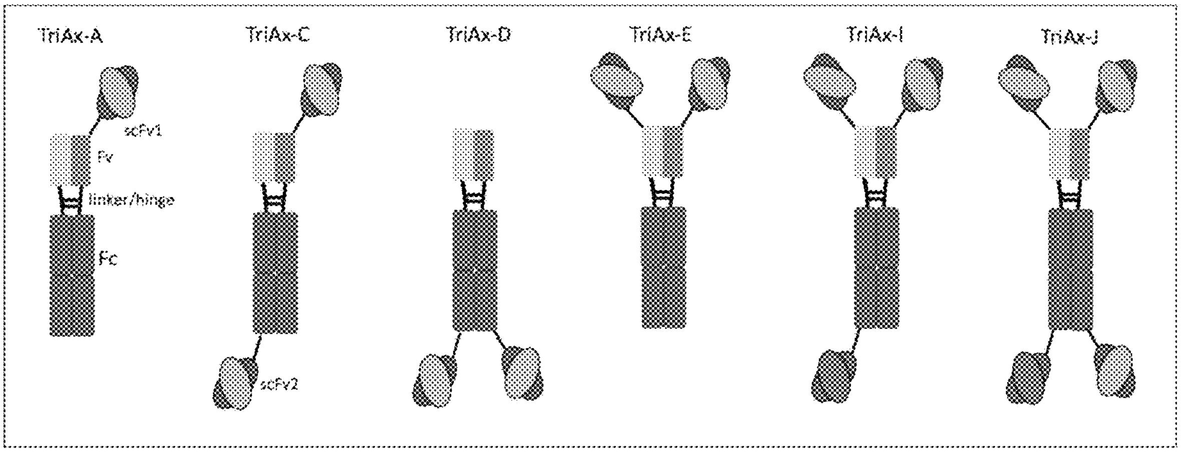
FIG. 1 depicts configurations of a class of multi-specific antibodies collectively named as TriAx for Tri-Axial antibodies, including but not limited to, TriAx-A, TriAx-C, TriAx-D, TriAx-E, TriAx-I, and TriAx-J antibodies.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

To enable immunotherapeutics for more effective cancer treatment, especially solid tumors, a combination therapeutic is paramount that incorporates multiple target specificities and/or mechanisms of action beyond that of typical bispecific antibodies. A therapeutic that is essentially a combination treatment such as that described here, is necessary to effectively treat cancer and to more frequently achieve a complete and durable response. Specifically, there is a need for a scaffold that possesses certain properties to create a combination therapeutic with advantageous mechanisms of action, manufacturing, pharmacokinetics, and low antigenic properties relative to approved bispecific antibodies. Many bispecific antibodies that are based on a whole antibody may have a greater mass relative to the tri-specific antibodies described here. While antibodies with a smaller mass, based on antibody fragments, may have greater tumor penetration, they generally possess relatively poor pharmacokinetic properties, such as FDA-approved bispecific antibody Blincyto that does not possess an Fc region. In addition, many bispecific antibodies are based on knob-into-hole possess mutations within the constant domains of the Ig structure, which may contribute to an anti-drug antibody (ADA) response. In this context, a group of modified antibodies described here as Tri-axial or TriAx antibodies, do not require mutations in any constant domain yet have multiple antigen binding specificities.

All formats of TriAx antibodies contain a characteristic core structure comprising a single paired VH and VL (Fv) that defines the first antigen binding specificity while also correctly driving the heterodimerization of the two Fc containing monomers. This core structure is stabilized through the formation of multiple disulphide bonds C-terminal to the Fv region. Minimally a third linker ("triaxial" core) is used to add at least one additional antigen binding region, such as an scFv. A second linker may be added for a second scFv, and so on to increase tumor cell binding specificity or regulate an immune response. These "TriAx" antibodies may be further modified with engineered proline-rich rigid peptide linkers to position binding domains for optimal ligand binding. TriAx antibodies may be composed entirely of human, humanized and low antigenic linker sequences to decrease risk of an ADA response.

TriAx antibodies are designed to bind two or more effector cell receptors to induce two or more mechanisms of anti-tumor activity, for example, T or NK mediated cytotoxicity (CD3, NKG2D), tumor cell phagocytosis (FcR, CR3, CR4, AXL, CD13, CD206) or apoptosis (DR5, i.e. death receptor 5), immune cell stimulation (CD40, OX40), immune checkpoint inhibition (PD-L1, TIGIT, PD1, CTLA4) or conversion of tumor associated macrophages (TAM) from immunosuppressive to inflammatory phenotype (CD206, TREM-2).

The TriAx platform allows for generation of TriAx-A, TriAx-C, TriAx-D, TriAx-E, TriAx-I, and TriAx-J antibodies as shown in FIG. 1. Multi-specific antibodies, namely, bi-, tri-, tetra-, and penta-specific antibodies can be generated according to these formats. The TriAx antibody core is characterized by a Fv region of paired VL and VH directly linked to a Fc domain in the absence of CH1, and the core can be formed and stabilized by pairing two asymmetric monomers, i.e. LC and HC monomers, via a disulfide bridge (Ig hinge or other linkers) (Table 1). This Fv-Fc core possesses at least one additional linker connecting to an antigen binding domain that binds to a target antigen/ligand. TriAx-A is a format of bi-specific antibodies with addition of one scFv domain covalently linked to the N-terminus of VH. TriAx-C is a format of tri-specific antibodies with addition of one scFv domain covalently linked to the N-terminus of VH and a second scFv domain to the C-terminus of a CH3 domain. TriAx-D is a format of tri-specific antibodies with addition of two different scFv domains at its C-terminus. TriAx-E is a format of tri-specific antibodies with addition of two different scFv domains at its N-terminus and linked to VL and VH, respectively. TriAx-I is a format of tetra-specific antibodies with addition of a third scFv domain to the C-terminus of Trix-E; and TriAx-J is a format of penta-specific antibodies with addition of a fourth scFv domain to the C-terminus of Trix-I. Other multi-specific antibody formats do not possess this TriAx core structure directing and covalently stabilizing this multi-specific heterodimer formation including, BiTE, DART-Fc, IgG-scFv, TandAb, DVD-Ig, CrossMab, Duobody, Fab-scFv-Fc, ADAPTIR, ImmTac, TriKE, scFv-scFv-scFv, CODV-Ig, Two-in-one, Tandem-scFv-Fc, scFv-Fc knobs-Into-holes, F(ab') 2, and scDiabody-Fc (Labrijn 2019, Yu 2017, Suurs 2019, and Bates 2019). In this context, the following examples illustrate that TriAx antibodies not only can be produced but also function with efficiency and stability as designed. The production of these TriAx antibodies suggest a greater percentage of correctly formed heterodimers relative to other modified antibodies, such as the types of knob-into-hole antibodies.

The terms "a", "an" and "the" as used herein are defined to mean "one or more" and include the plural unless the context is inappropriate.

The term "antibody" is used in the broadest sense and specifically covers single monoclonal antibodies (including agonist and antagonist antibodies), antibody compositions with polyepitopic specificity, as well as antibody fragments, such as Fab, F(ab') 2, and Fv, so long as they exhibit the desired biological activity. In some embodiments, the antibody may be monoclonal, chimeric, single chain, multi-specific, multi-effective, human and humanized antibodies. Examples of active antibody fragments that bind to known antigens include Fab, F(ab')2, scFv, and Fv fragments, as well as the products of a Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind to an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain moiety is comprised of a light chain moiety variable domain (abbreviated as VL) and a light chain moiety constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the heavy and light chain there are binding regions that interacts with the antigen.

The term "multi-specific" antibody as used herein denotes an antibody that has at least two binding sites each having a binding affinity to an epitope of an antigen. The term "bi-specific, tri-specific, tetra-specific, or penta-specific" antibody as used herein denotes an antibody that has two, three, four, five, or six antigen-binding sites.

The term "humanized antibody" antibody refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art (see Queen et al., Proc. Natl Acad Sci USA, 1989; Hodgson et al., Bio/Technology, 1991). In one embodiment, the "humanized antibody" may be obtained by genetic engineering approach that enables production of affinity-matured humanlike polyclonal antibodies in large animals such as, for example, rabbits (see U.S. Pat. No. 7,129,084).

The term "antigen" refers to an entity or fragment thereof which can induce an immune response in an organism, particularly an animal, more particularly a mammal including a human. The term includes immunogens and regions thereof responsible for antigenicity or antigenic determinants.

The term "epitope", also known as "antigenic determinant", is the part of an antigen that is recognized by the immune system, specifically by antibodies, B cells, or T cells, and is the specific piece of the antigen to which an antibody binds.

The term "immunogenic" refers to substances which elicit or enhance the production of antibodies, T-cells, or other reactive immune cells directed against an immunogenic agent and contribute to an immune response in humans or animals. An immune response occurs when an individual produces sufficient antibodies, T-cells, and other reactive immune cells against administered immunogenic compositions of the present application to moderate or alleviate the disorder to be treated.

The term "tumor antigen" as used herein means an antigenic molecule produced in tumor cells. A tumor antigen may trigger an immune response in the host. In one embodiment, the tumor cells express tumor antigens, including without limitation, tumor-specific antigens (TSA), neoantigens, and tumor-associated antigens (TAA).

The term "specific binding to" or "specifically binds to" or "specific for" a particular antigen or an epitope as used herein means the binding that is measurably different from a non-specific interaction. Specific binding can be measured by determining binding of a molecule compared to binding of a control molecule, which generally is a molecule of similar structure that does not have binding activity. Specific binding can be determined by competition with a control molecule that is similar to the target. Specific binding for a particular antigen or an epitope can be exhibited by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$, alternatively at least about $10^{-10}$ M, at least about $10^{-11}$ M, at least about $10^{-12}$ M, or greater, where KD refers to a dissociation rate of a particular antibody-antigen interaction. In some embodiments, a multi-specific antibody that specifically binds to an antigen will have a KD that is 20-, 50-, 100-, 500-, 1000-, 5,000-, 10,000- or more times greater for a control molecule relative to the antigen or epitope. Also, specific binding for a particular antigen or an epitope can be exhibited by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

EXAMPLES

The present disclosure is further described with reference to the following examples. These examples are provided for purposes of illustration only and are not intended to be limiting unless otherwise specified. Those of skill in the art will readily recognize a variety of non-critical parameters that could be changed or modified to yield essentially the same or similar results.

Example 1. Characteristic Features of TriAx Antibodies

TriAx antibodies are heterodimers that are characterized by a Fv-Fc core structure comprised, from N- to C-terminus, of a Fv region, a modified Ig hinge, and an Ig Fc region as shown in FIG. 1. The additional binding domains may be a scFv, a scFab, a Fab, a single domain VH, or a natural protein fragment.

The TriAx core components include two linkers (e.g. a glycine rich linker fused to a truncated Ig hinge) covalently linking both VH and VL chains of the Fv to the CH2-CH3 monomers. This glycine rich flexible linker to Ig hinge may facilitate efficient VH-VL pairing. The TriAx binding domains may be attached by a flexible glycine rich linker, such as SEQ ID NO: 18, or a more rigid proline-rich linker, such as SEQ ID NO: 21. Linkers may typically be 4 to 7 residues in length. The TriAx Fc may be composed of an IgG1 hinge or an IgG4 hinge with a S228P substitution. The first seven N-terminal amino acids of the IgG1 hinge, EPKSCDK, may be replaced with a glycine rich linker, such as SEQ ID NO: 22 or SEQ ID NO: 18. Hinge residues at position 234 and 235 (G1 numbering) may be LL, FL, or AA to regulate the degree of FcR binding (Saunders 2019). The CH2 and CH3 domains may be all IgG1 or IgG4 or a combination, such as G1 CH2 and G4 CH3. A TriAx molecule may possess a CH3 with substitutions to produce a knob-into-hole (Merchant 1998).

Built on the central TriAx Fv-Fc core structure, TriAx-A is a bivalent antibody format with a single scFv linked to either VH or VL of the Fv, such as h10Ta, h5Ta, h8Ta, and hB2Ta antibodies, whose structural features were listed in Table 1. TriAx-C is a format of trivalent antibody format with the addition of one scFv to the N-terminus of the VH or VL and a second scFv or a protein binding domain at the C-terminus of either CH2-CH3 monomer, such as hC3dh10Tc antibody whose structural features were listed in Table 1. TriAx-D is a trivalent with an scFv linked to the C-terminus of each CH3 of the Fv-Fc core, such as h8C3dTa antibody, whose structural features were listed in Table 1. TriAx-E is a trivalent antibody format with two scFv linked to the VH and VL of the Fv-Fc core, respectively. Examples of TriAx-E antibodies, such as h10Te, h8Te, and h8h10Te, were listed in Table 1 for their structural features and sequence ID. TriAx-I is a format of tetravalent antibodies with the addition of one scFv at the N-terminus of each VH and VL plus one scFv at the C-terminus of either CH2-CH3 monomer. TriAx-J is a pentavalent format with the addition of one scFv at the N-terminus of each VH and VL and at the C-terminus of each CH2-CH3 monomer.

Figure 2:
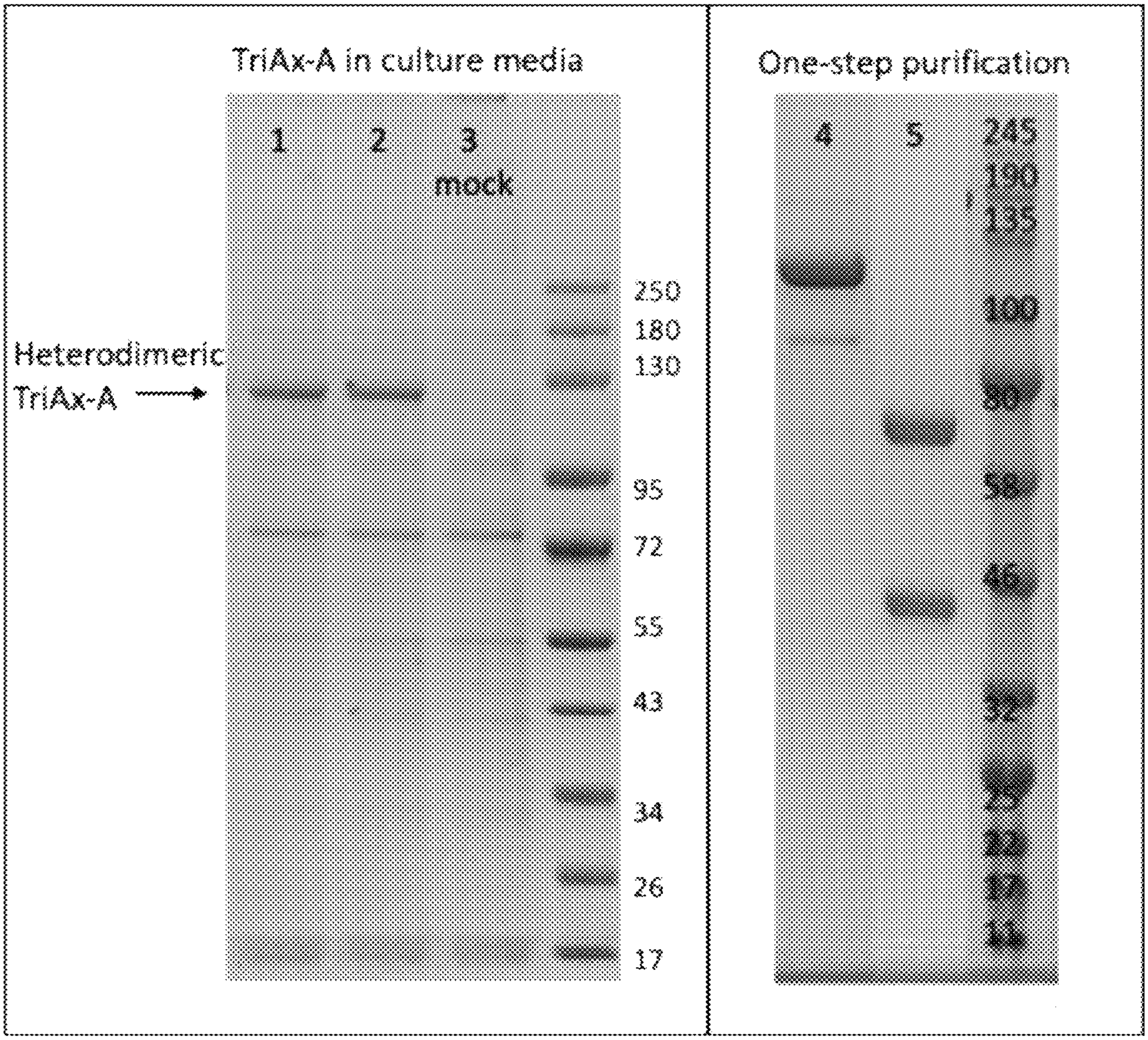
FIG. 2 shows the production, heterodimerization, and purification of TriAx-A antibodies.

Example 2. TriAx-A Antibodies h8Ta is a TriAx-A bi-specific antibody targeting both TROP2 and CD3 (SEQ ID NO: 1 and 4, also see Table 1). TROP2 is a transmembrane glycoprotein that is deregulated in all cancer types independent of baseline levels of TROP2 expression. TROP2 is an ideal candidate for targeted therapeutics. Several TROP2-targeted antibody therapeutics in early-phase clinical trials have demonstrated safety and clinical benefit for treating triple-negative breast cancer, platinum-resistant urothelial cancer, and small-cell lung cancer.

h8Ta was produced in HEK293 cells by PEI co-transfection of a plasmid for heavy (core Fv VH) and light (core Fv Vk) chains. At day 3 post transfection, a sample of culture media was subjected to SDS-PAGE, as shown in FIG. 2; transfected cell media (lanes 1 and 2), mock transfected media (lane 3). Following a one step, protein-A purification, h8Ta antibody was subjected to SDS-PAGE under non-reducing and reducing conditions as shown in FIG. 2 lane 4 and 5, respectively. Under non-reducing conditions this TriAx-A antibody migrates as a ~116 kDa protein consistent with its calculated heterodimeric size. Under reducing conditions, the heavy chain is ~70 kDa and the light chain is ~44 kDa, consistent with their calculated sizes. The efficiency of heterodimerization was approximately 90% or greater. There are no other significant TriAx products or fragments detectable when compared to the mock control media. These TriAx-A may possess linkers of different length and composition and Fc sequence to modify FcR binding and circulatory half-life.

Example 3. TriAx-C Antibodies

Two TriAx-C antibodies were generated with their binding specificity to a phagocytic receptor CR3. h10Cd3Tc is a TriAx-C tri-specific antibody targeting CDH17, CR3, and CD3 (SEQ ID NO: 7 and 8). h8C3dTd is a TriAx-D trispecific antibody targeting TROP2, CR3 and CD3 (SEQ ID NO: 9 and 10). Both TROP2 and CDH17 are prominent cancer biomarkers characterized by their overexpression in various forms of solid tumors including stomach, colon, pancreatic, liver and liver. CDH17 is highly expressed in metastatic cancers, and the blockage of CDH17 expression and functions can markedly reduce lung metastasis of hepatocellular carcinoma (HCC). Both anti-CDH17 monoclonal antibody and anti-CDH17/CD3 bi-specific antibody display the growth inhibitory effect on liver and stomach tumor cells (see Applicant's application WO/2019/222428, incorporated herein in its entirety). CR3 or complement receptor 3 is a heterodimer of α (CD11b) and β (CD18) transmembrane glycoproteins. The I-domain containing alpha integrin combines with the beta 2 chain (ITGB2) to form a leukocyte-specific integrin referred to as macrophage receptor 1 ('Mac-1'), or inactivated-C3b (iC3b) receptor 3. During the process of opsonization, C3d is deposited on target cell surfaces where it serves as a macrophage CR3 ligand for phagocytosis. A binding to CR3 via either its ligand, such as C3d, or an activating antibody, may direct a major phagocytic receptor to tumor cells and broadly induce tumor cell phagocytosis and pro-inflammatory macrophage polarization. In this context, the TriAx-C antibodies, such as h8C3dTd and h10C3dTc, can bind either TROP2, CDH17, or both on tumor cells, which then present C3d for macrophage CR3 dependent phagocytosis. The TriAx-C antibodies may also engage FcR, which may further activate and enhance macrophage CR3 tumor cell phagocytosis. These TriAx-C antibodies may broadly target different tumor types enabling greater efficacy and safety relative to targeting a CD47 or CD24 phagocytic checkpoint.

Figure 3:
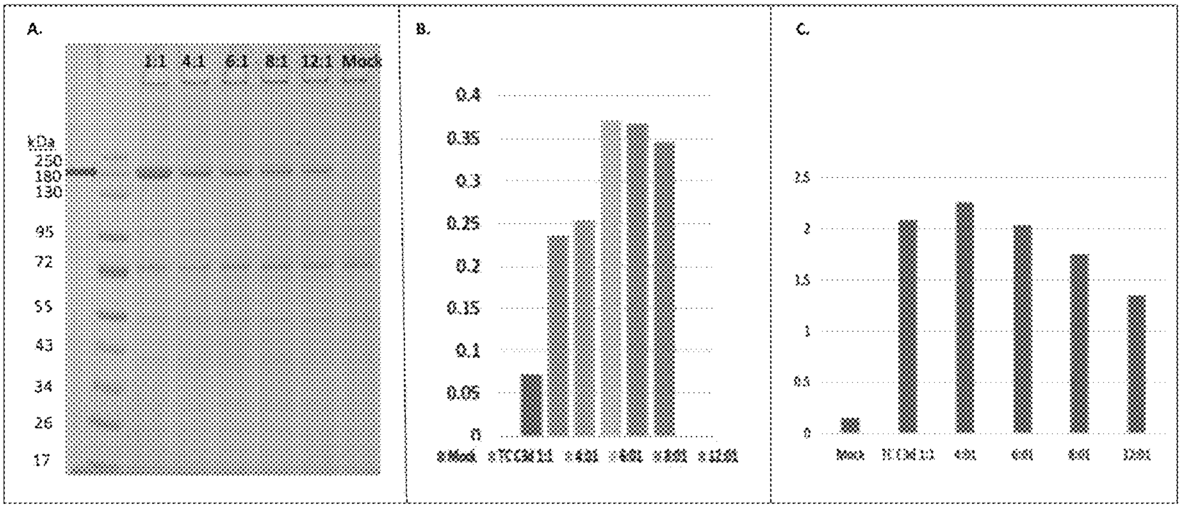
FIG. 3, including

In addition to the anti-CD3 Fv and anti-CDH17 scFv domains, h10Cd3Tc comprises C3d as a CR3 binding domain. When expressed in HEK293 cells, the heavy (core Fv Vh) and light chains (core Fv Vk) of h10Cd3Tc were co-transfected at ratios of 1:1, 4:1, 6:1 and 12:1 (Vh:Vk). Three days post-transfection the levels of antibody expression were determined by Octet (BLI). Production levels were 104 ug/ml (1:1), 27.3 ug/ml (4:1), 22 ug/ml (6:1), 21.7 ug/ml (8:1), and 14.6 ug/ml (12:1). Production culture media samples were subjected to SDS-PAGE. As shown in FIG. 3A, the molecular weight of h10C3dTc was approximately 180 kDa, that is somewhat larger than the calculated weight of ~150 kDa. No other significant TriAx products or fragments were detected when compared to the mock control media. As both heavy and light chain monomers of h10Cd3Tc are of similar size, formation of homodimers cannot be readily distinguished by standard SDS-PAGE. When the concentrations were all adjusted to 5 ug/ml in an ELISA for quantifying the binding to immobilized CR3 I domain, the I-domain binding reached the peak when the plasmid ratio was 6:1 (FIG. 3B). The OD value in the ELISA was low due to low affinity of C3d binding to I domain (~400 nM). But the peak binding was approximately 7-fold greater than that of control media from mock transfected HEK293. The binding of h10C3dTc to CDH17 and CD3 was determined in an ELISA in which the sample antibody binds to a soluble form of CD3 followed by immobilized CDH17, and subsequently, an HRP conjugate that binds to the recombinant CD3. As shown in FIG. 3C, a plasmid ratio of 4:1 led to the peak binding, indicating that optimal heterodimerization may occur when the plasmids are co-transfected at certain ratios into HEK293 cells. The binding activity as shown in ELISA indicates that the tri-specific TriAx-C antibodies can be produced. These TriAx-C antibodies may possess linkers of different length and composition and Fc sequence to modify FcR binding and circulatory half-life.

Example 4. Thermal Stability of TriAx Antibodies

Figure 4:
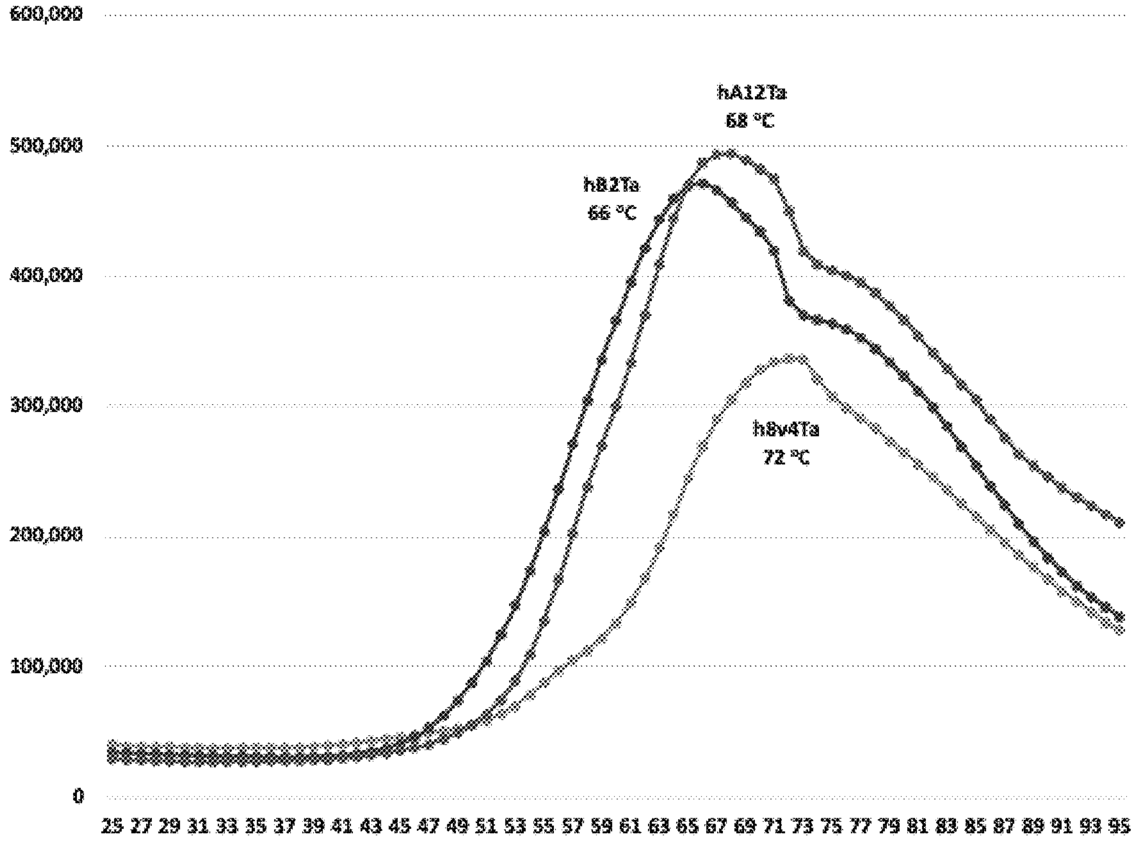
FIG. 4 demonstrates the thermal stability of TriAx antibodies.

The thermal stability of TriAx antibodies was determined in a thermal shift assay using SYPRO orange (King et al. 2011). The TriAx-A antibodies, such as h8Ta (SEQ ID NO: 1 and 4), hB2Ta (SEQ ID NO: 1 and 5), and hA12Ta (SEQ ID NO: 1 and 6) (see Table 1), were analyzed. These TriAx-A antibodies in PBS were centrifuged in a microfuge for 10 minutes, and the concentration was adjusted to 5 uM. A mixture of TriAx-A (50 ul) and SYPRO orange (1 ul) (125× in PBS; 2.5× final) were transferred to an optically clear 96 well plate for assay in a qPCR instrument. The temperature was increased from 25° C. to 99° C. at the rate of 1° C. per minute with a one-minute hold for each measurement with an excitation at 470 nm and emission at 586 nm. FIG. 4 shows an initial unfolding peak at 66° C. (hB2Ta), 68° C. (hA12Ta), and 72° C. (h8Ta), indicating that the TriAx platform antibodies are sufficiently stable for further development.

Example 5. Redirected T Cell Cytotoxicity of a TriAx-A Antibody Targeting TROP2 and CD3

Figure 5:
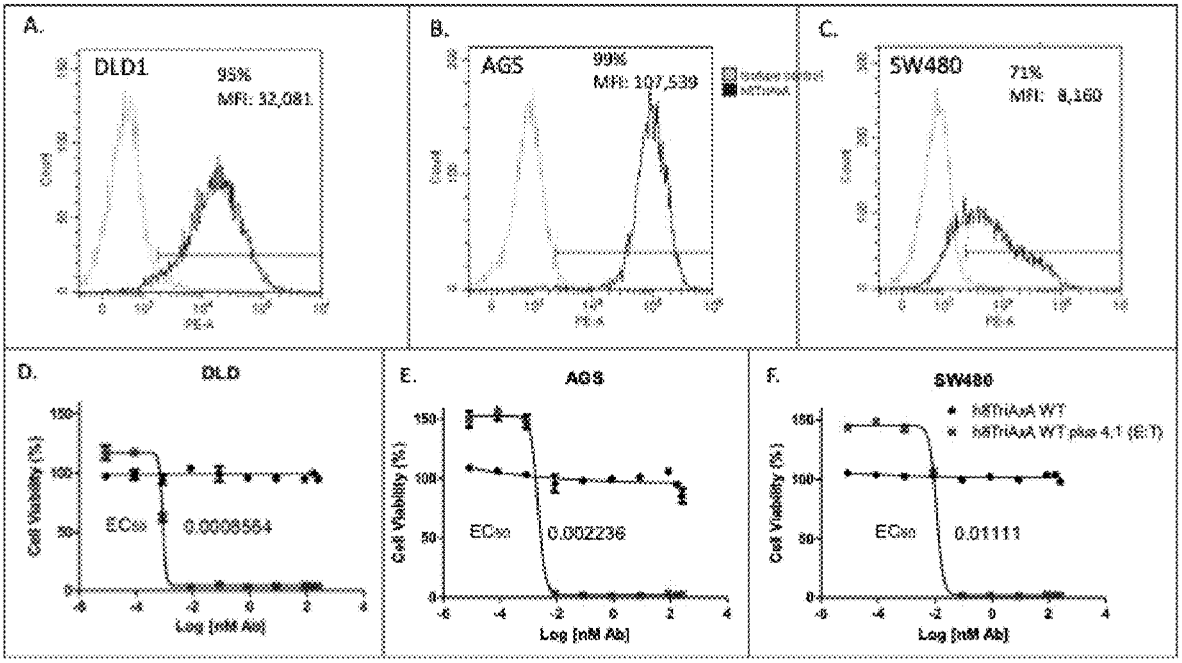
FIG. 5, including

To evaluate the function of TriAx platform antibodies, h8Ta, a TriAx-A bi-specific antibody (see Example 2), was assessed for redirected T cell cytotoxicity. Three luciferase-expressing GI tumor cells lines, DLD1 (colorectal cancer), SW480 (colorectal cancer) and AGS (gastric cancer), were used in a 24-hour assay with an E:T ratio of 4. Following a wash to remove dead cells, viable cells were quantitated using Bio-Glo (Promega) and a multimode plate reader. As shown in FIG. 5 (upper panel), h8Ta was used in a flow cytofluorimetry analysis to detect the expression of TROP2 in all three tumor cell lines (FIGS. 5A, 5B, and 5C). In the absence of T cells, cell viability did not decrease over the concentration range of the h8Ta antibody. In the presence of T cells, the EC50 values for h8Ta antibody-dependent tumor cell killing were determined at 0.8 pM for DLD, 2 pM for AGS, and 11 pM for SW480 (FIG. 5 lower panel, 5D, 5E, and 5F). The lower EC50 value of SW480 seems to correlate with its lower level of TROP2 expression. Thus, this bi-specific TriAx-A antibody can mediate potent, sub-pM tumor cell killing.

Example 6. Redirected T Cell Cytotoxicity of a TriAx-A Antibody Targeting FAP and CD3

Fibroblast activation protein alpha (FAP) is a 97 kDa, type II cell surface glycoprotein belonging to the serine protease family. In the colorectal cancer (CRC) metastases, the fibroblast activation protein-alpha (FAPα) plays a critical role. It has been reported that in all CRC samples examined, FAPα was expressed in cancer-associated fibroblasts, but not in normal colon, hyperplastic polyps, or adenoma samples.

Figure 6:
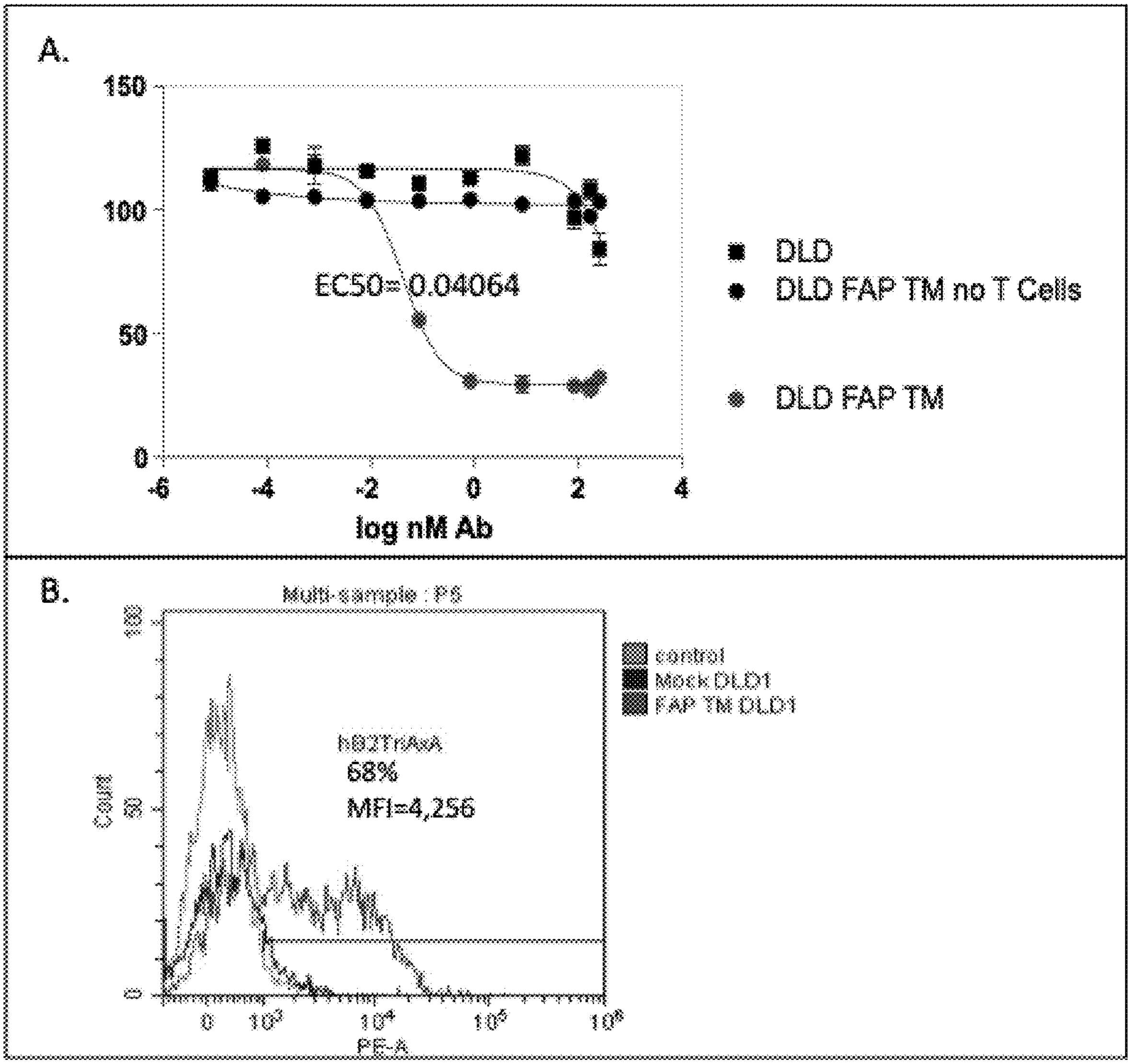
FIG. 6, including

A TriAx-A bi-specific antibody, hB2Ta (SEQ ID NO: 5 and 6), was generated to target both CD3 (via Fv) and FAP (via scFv). To determine its redirected T cell cytotoxicity activity, FAP mRNA was electroporated into DLD1 cells (DLD1-FAP) that also express luciferase. The following day a microtiter plate cytotoxicity assay was initiated with and without expanded T cells (E:T of 4). After the addition of the antibody at an experimental concentration range in a mixture with either DLD1 or DLD1-FAP, the assay was incubated for 24 hours, followed by a wash, an addition of Bio-Glo substrate and a multimode plate reader that measures the luciferase activity. As shown in FIG. 6A, h1B2Ta mediated a concentration dependent tumor cell cytotoxicity in the presence of T cells and DLD1-FAP (EC50=41 pM), whereas such cytotoxicity was not detected or unsubstantiated in the absence of FAP-expressing tumor cells or T cells. The FAP expression in DLD1 cells was determined by flow cytofluorimetry at the time the assay was initiated (FIG. 6B). The percentage of DLD1 cells expressing FAP at 68% (MFI=4,256) seems to be correlated with the maximal cytotoxicity of ~70%. Thus, the TriAx antibody with a binding specificity for FAP effectively kills tumor cells with low FAP expression.

Example 7. L4, a Low Affinity Anti-CD3 Binding Domain

To reduce the risk of off-tumor T cell signaling and the sink to T cells and lymphoid tissues, a low affinity monovalent CD3 binding region, L4 (SEQ ID NO: 13), was introduced into TriAx platform antibodies. CDRs of UCHT1 Vh and Vk (Shalaby 1992) were partially or completely replaced with human germline sequences to generate low affinity and low antigenic anti-CD3 variants. Substitution of Vk CDR1 with IGKV1-33*01 germline sequence resulted in a lower affinity mutant L4, which was incorporated into the core Fv of several TriAx antibodies. Thus, the amino acid sequence of this anti-CD3 variant comprises UCTH1CDR sequences except for CDRL1 substitutions, R24Q and R30S, as indicated in FIG. 7.

Example 8. T Cell Affinity and Activation Mediated by a TriAx Antibody Possessing L4

Figure 8:
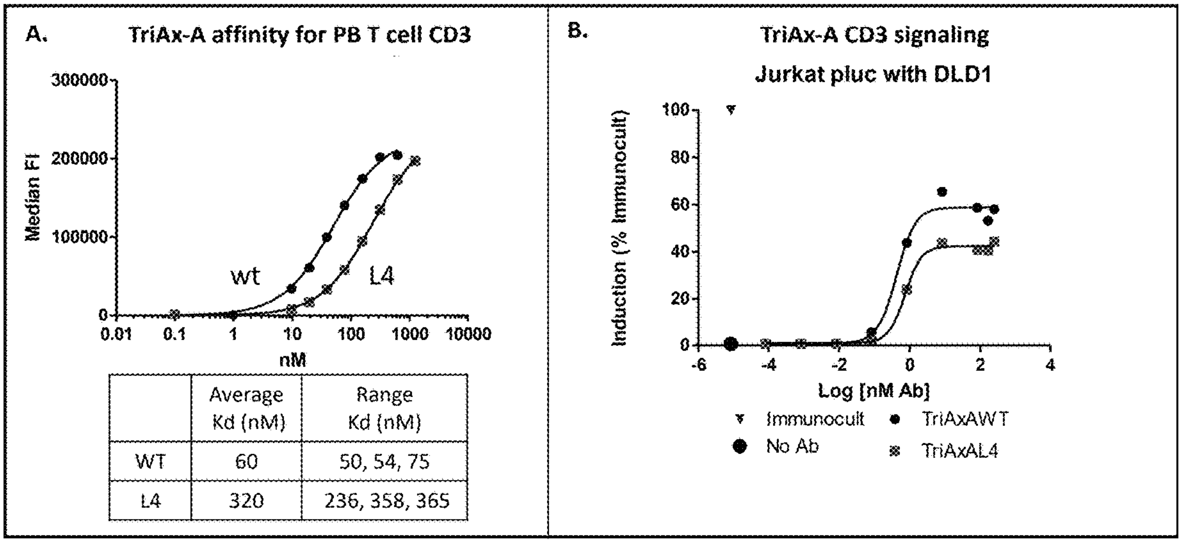
FIG. 8, including

To assess their ability for T cell affinity and activation, the TriAx antibodies having either L4 or its parental Fv Vk CDR1 ("wt") was determined by flow cytofluorimetry, namely, h10Ta-L4 (SEQ ID NO: 1 and 2) and h10Ta-wt. The antibody binding to peripheral blood T cells was determined for T cell affinity over a range of concentration as shown in FIG. 8A. MFI were plotted and affinity (EC50) was determined using GraphPad PRISM. Three independent affinity determinations and their averages were indicated. The result indicates that the modified CDRL1 in L4 (320 nM) is responsible for a 5-fold decrease in T cell affinity relative to the parental Fv (60 nM). T cell signaling was determined using a T cell line possessing an NFAT inducible promoter for luciferase expression (Jurkat Promega kit NFAT J1621). Both h10Ta antibodies engaged CDH17 (on DLD1) and CD3. The signaling was determined according to manufacturer's protocol, at 24 hours using an antibody concentration range as indicated and Jurkat reporter cells at $100\times10^3$ and DLD1 cells at $30\times10^3$ per microtiter well (96-well plate). Luciferase expression/activity was measured using a multimode plate reader. As shown in FIG. 8B, h10Ta-L4 had a 2-fold decrease in T cell signaling relative to h10Ta-wt with the parental Fv. Controls included no antibody or a CD3, CD28, CD2 agonist (Immunocult; StemCell) to induce maximal stimulation.

Example 9. Tumor Cell Cytotoxicity Mediated by a TriAx Antibody Possessing L4

Figure 9:
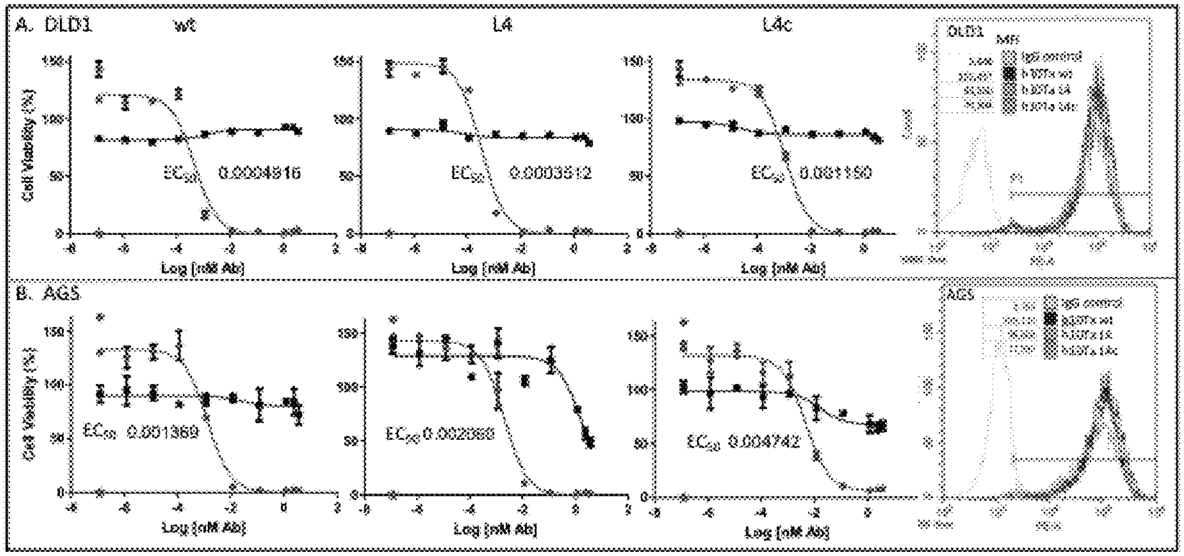
FIG. 9, including

Redirected T cell cytotoxicity was determined for both h10Ta-L4 and h10Ta-wt. In addition, h10Ta-L4c, which was derived from h10Ta-L4 by harboring Vk ACys43 and Vh Q114C substitutions in order to create a stabilizing interdomain disulfide, was included in the test. T cell killing of a luciferase expressing colon cancer cell line DLD1, and gastric cancer cell line, AGS, was determined over a range of antibody concentrations in a 24-hour assay with an E:T ratio of 4. Following a wash to remove dead cells, viable cells were quantitated using Bio-Glo (Promega) and a multimode plate reader. In the presence of T cells, the EC50 for killing DLD1 was 0.5 pM for h10Ta-wt, 0.4 pM for h10Ta-L4, and 1.2 pM for h10Ta-L4c. The EC50 for AGS killing was 1.4 pM for h10Ta-wt, 2 pM for h10Ta-L4, and 4.7 pM for h10Ta-L4c. These results presented in FIG. 9 demonstrate that the lower affinity to CD3 in L4 did not significantly decrease cytotoxic activity as determined in this assay. As to the TriAx antibody possessing L4c, the result indicates a slight decrease in cytotoxic activity relative to the antibody having the parental L4, suggesting that the interdomain disulfide may exert a negative positional effect by altering a CDR residue position that is involved in CDH17 binding.

Figure 10A:
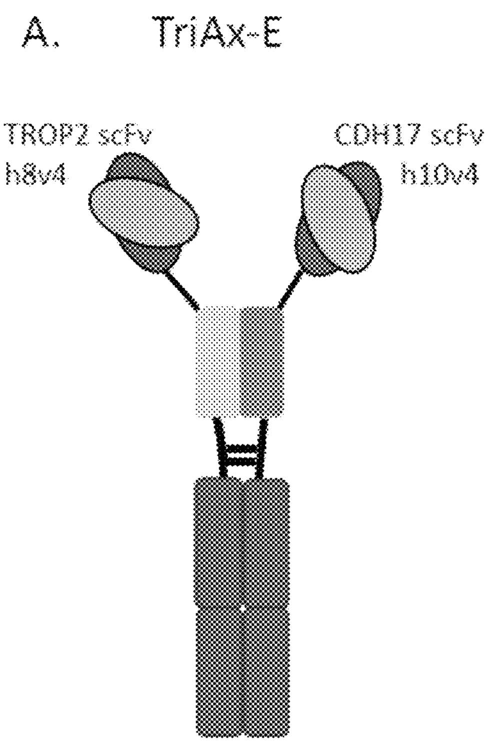
FIG. 10, including FIGS. 10A-10C demonstrates the binding specificities of and redirected T cell cytotoxicity by TriAx-E antibodies.
Figure 10B:
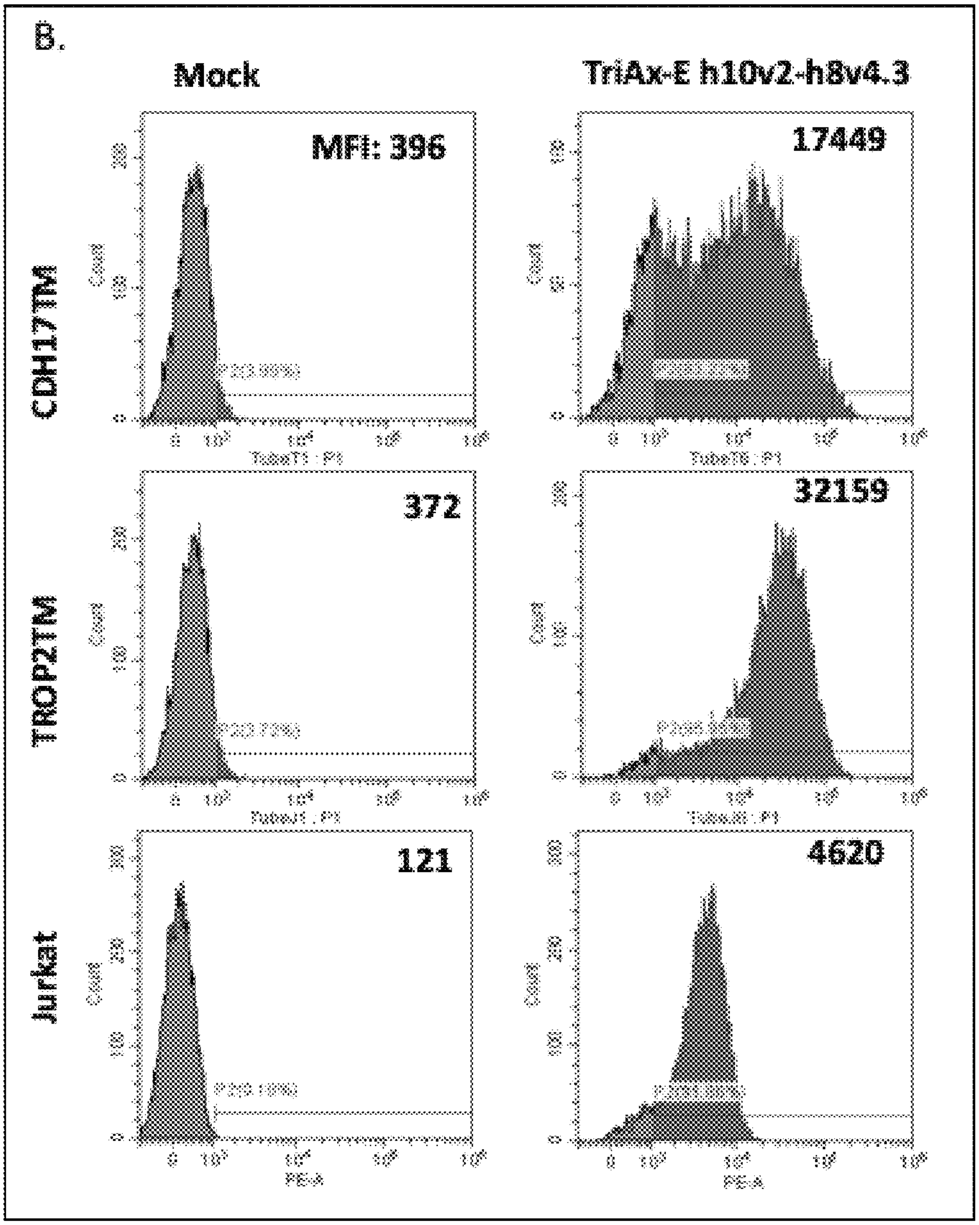
Figure 10C:
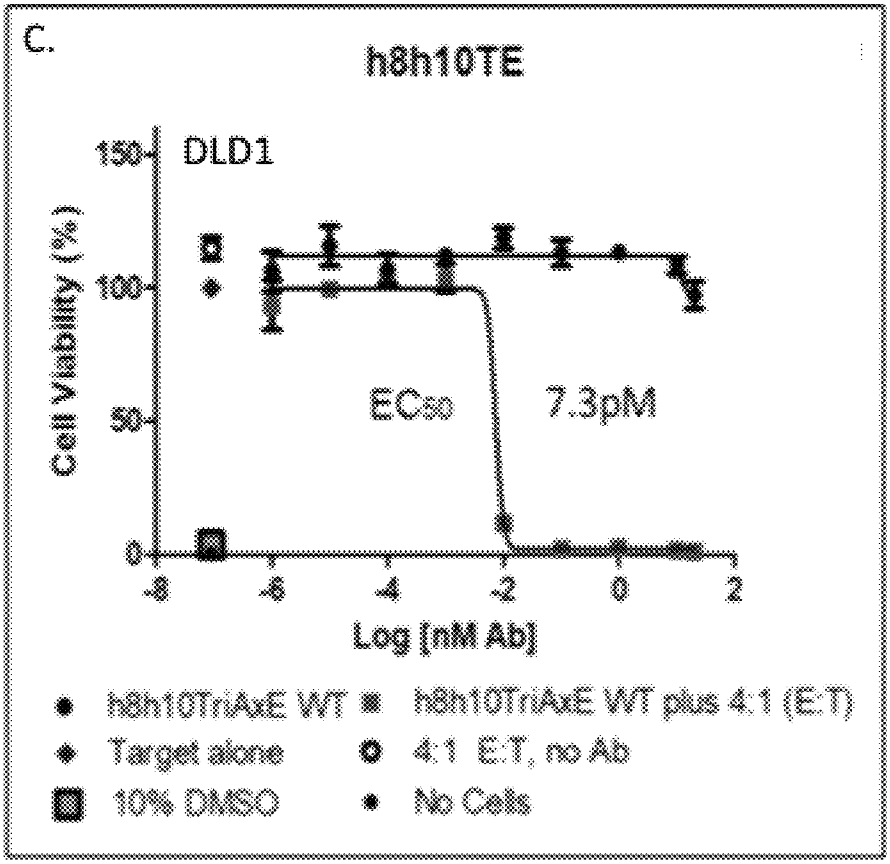

Example 10. TriAx-E Antibodies h8h10Te (SEQ ID NO: 12 and 2) is a TriAx-E tri-specific antibody comprising both anti-TROP2 (h8) and CDH17 (h10) scFv binding domains at N-terminal of the anti-CD3 core Fv (Table 1). The binding of h8h10Te antibody (possessing the parental anti-CD3 Fv) to all three antigens was demonstrated by flow cytofluorimetry. FIG. 10 shows that h8h10Te specifically bound to HEK293 transfectants expressing transmembrane forms of either CDH17 or Trop2. h8h10Te also bound specifically to Jurkat cells that express CD3. Thus, the TriAx-E tri-specific antibodies can be generated and are capable of binding to all 3 target antigens. TriAx-E function is described in FIG. 10. h8h10Te, supports potent redirected T cell killing of DLD1 tumor cells in a 24 hr cytotoxicity assay using a E:T ratio of 4.

Example 11. The Steric Effect of Multi-Specific TriAx Antibodies

Figure 11:
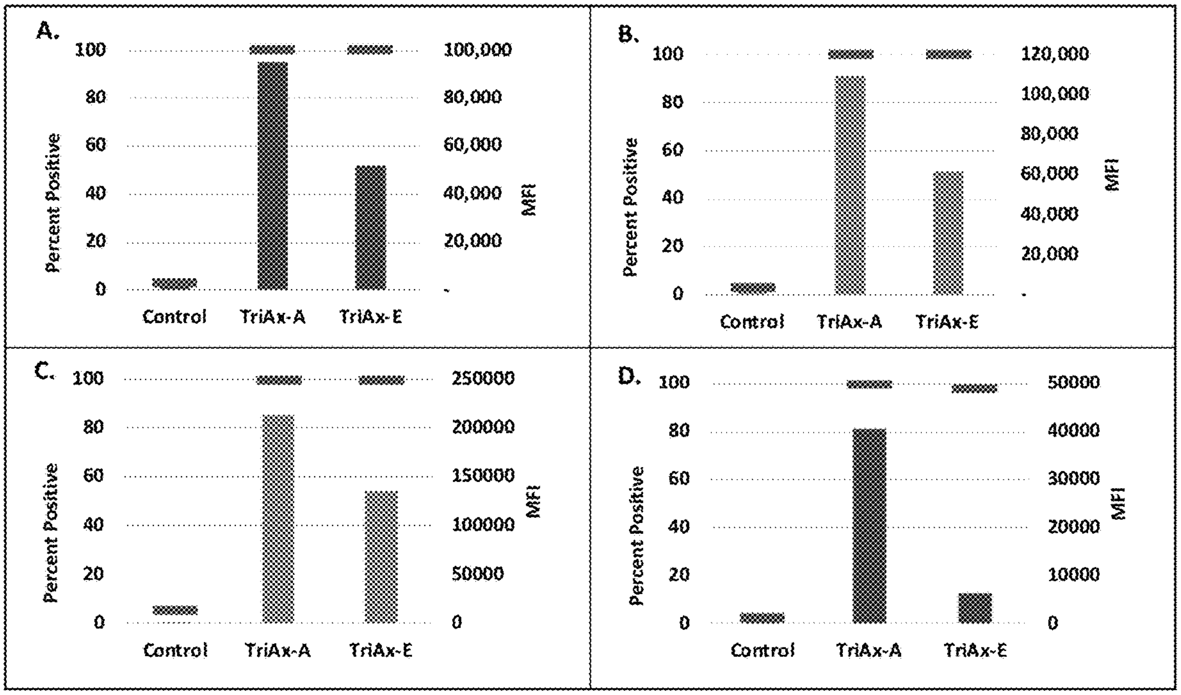
FIG. 11, including

With the anti-CD3 binding domain at the Fv position of the TriAx core structure, the addition of one or more binding domains, such as scFv domains, may affect the efficacy of the antibody to bind to cellular CD3. In this regard, TriAx-A antibody, h10Ta (SEQ ID NO: 1 and 2), and a TriAx-E antibody, h10Te, possessing identical anti-CD3 Fv region (wt), were used for comparison. The activity of binding to CD3 was determined by flow cytofluorimetry using 5 ug/ml of each TriAx antibody. FIG. 11 shows that, relative to the binding of the TriAx-A antibody, the binding of the TriAx-E antibody was decreased by approximately 2 to 6-fold (median fluorescent intensity; MFI). Decrease binding to the anti-CD3 Fv as the TriAx-E core is likely the result of steric inhibition. TriAx formats with an scFv linked to the core Fv Vh and Vk as TriAx-E, such as TriAx-I and TriAx-J, may also demonstrate decreased binding to CD3 or other core Fv specificity. Relative to certain other formats administration of these TriAx antibodies may result in less sink to T cells or lymphoid tissue and greater biodistribution to tumor tissue. This structure may therefore provide greater tumor microenvironment (TME) localized activity, greater efficacy and safety. A TriAx-A or TriAx-C format, possessing a single N-terminal scFv and hence a smaller N-terminal mass however, may enable more efficient binding to a tumor antigen relative to a TriAx-E or a typical whole antibody.

Example 12. Stabilized scFv (LocV) in TriAx Antibodies

Figure 12:
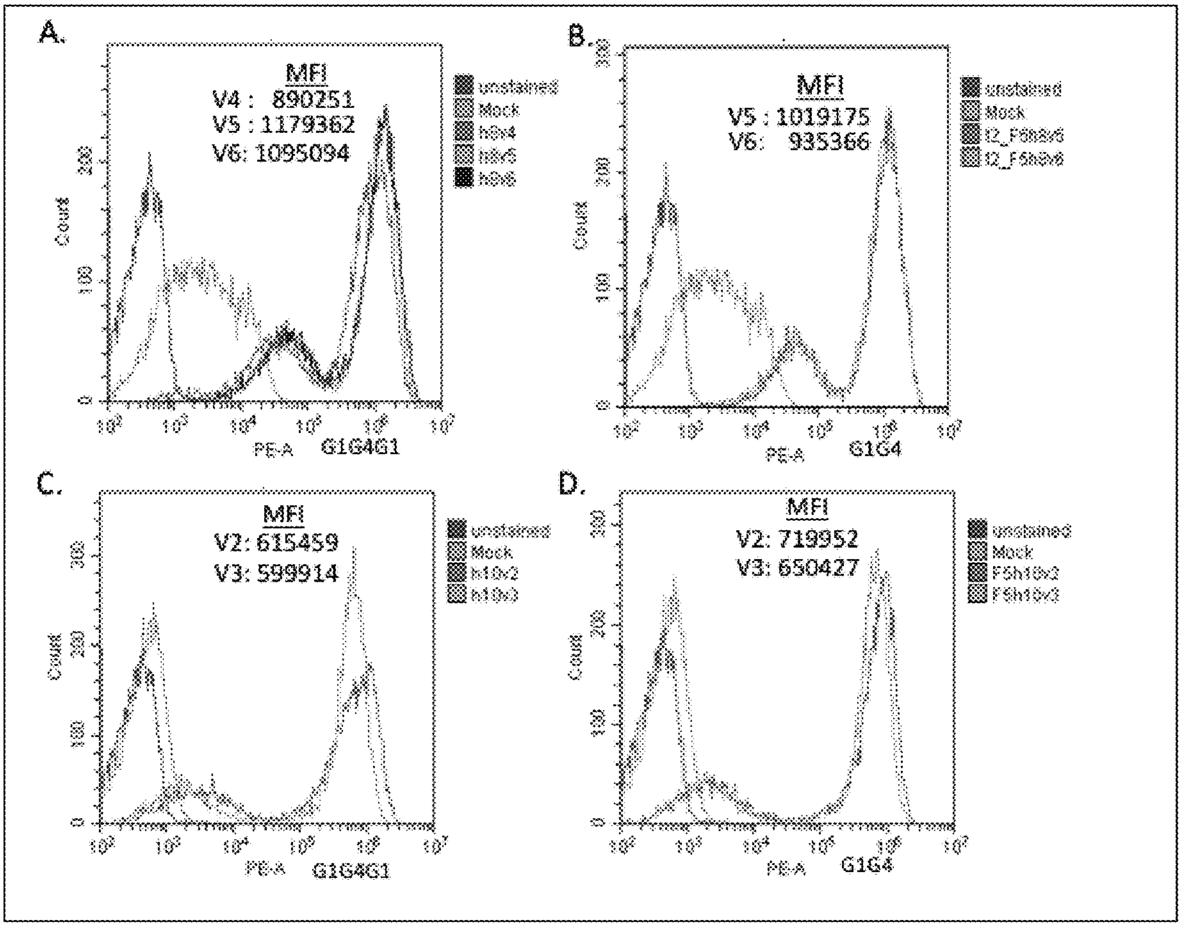
FIG. 12, including

Stabilized versions of TriAx-A scFv specific for TROP2 (h8v5 and h8v6) or CDH17 (h10v3) were generated by back mutating framework residues of the humanized versions h8v4 and h10v2, to enhance the Vh-Vk interface (h8v5, h8v6 and h10v3) and by substituting two residues with cysteine within the Vh domain to create a second disulfide bond (h8v6) (Ewert 2004, McConnell 2012, Weatherill 2012). As shown in FIG. 12, these humanized and humanized-stabilized versions were expressed with either Fc: G1G4G1 (A and C) or Fc: G1G4 (B and D) in HEK293 cells. Binding to CDH17 and TROP2, which was expressed in HEK293 cells by standard PEI-transfection, was determined by flow cytofluorimetry using 5 ug/ml of each TriAx. The level of binding (MFI) of h8v4, v5 and v6 were similar (A and B). The binding of h10v2 and v3 was also similar (C and D). The data indicates that the substitutions generated for scFv stabilization did not have a significant negative structural impact. Instead, stabilized scFv (LocV) improves the binding of TriAx antibodies to tumor antigens.

Example 13. Stabilized Low Antigenic Linkers

Figure 13:
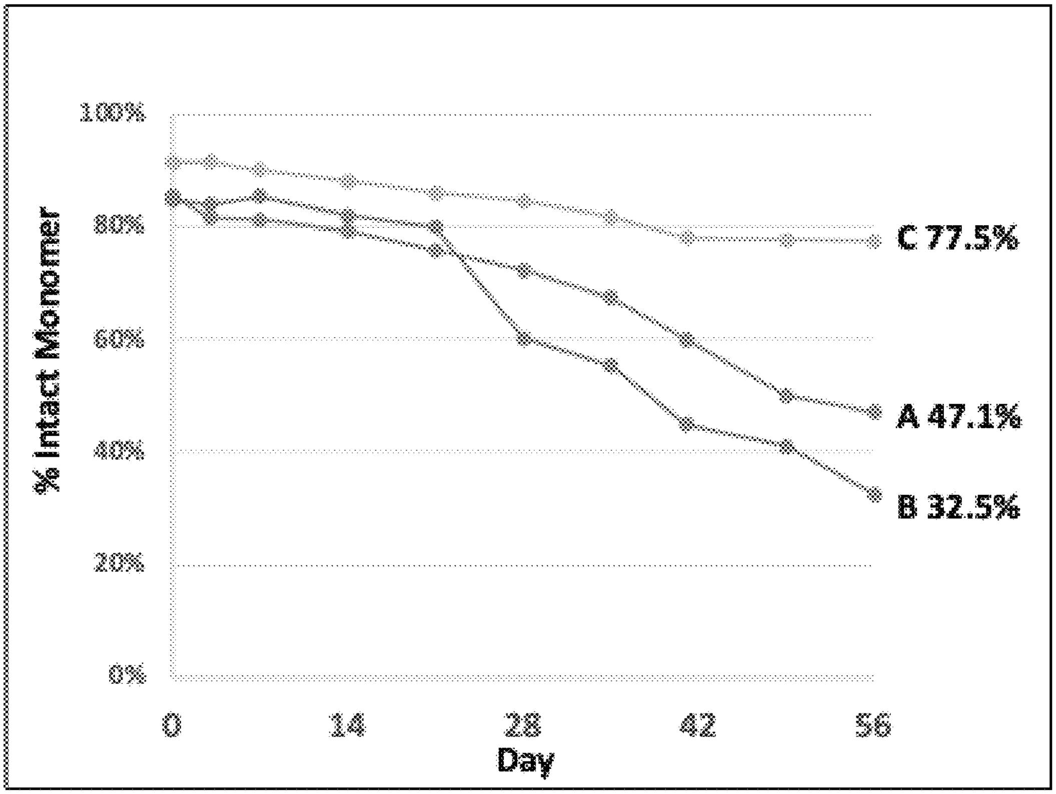
FIG. 13 depicts stabilized low antigenic linkers in TriAx antibodies.

ARB202, a bispecific antibody specific for CDH17 and CD3 with an IgG-scFv format (see Applicant's application WO/2019/222428, incorporated herein in its entirety), was used to compare the stability of 3 proline rich linkers: A=-SEQ ID NO: 19, B=-SEQ ID NO: 20 and C=SEQ ID NO: 21. The linkers extend from the C-terminus of Fc to the N-terminus of anti-CD3 scFv domain. The bispecific antibody (1 mg/ml) was stored at 37° C. in 10 mM histidine buffer, pH6.0 for 56 days. At the indicated time points a sample was analyzed for degradation by UPLC. As shown in FIG. 13, Linker C conferred greater stability (77.5%) relative to Linker A (47.1%) and Linker B (32.5%). In binding and signaling assays the function of the three bispecific antibodies were equivalent at day 0 and after 14 days in plasma at 37° C. Thus, Linker C enables greater stability without decreasing function.

Example 14. TriAx-I and TriAx-J Antibodies h8h10B2Ti (SEQ ID NO: 14 and 15) is an example of tetra-specific TriAx-I antibodies comprising binding specificities to tumor associated antigens, TROP2, CDH17, and FAP (expressed on cancer associated fibroblasts, or CAF). This TriAx-I antibody also binds to CD3 to trigger T cell directed killing of GI cancer cells expressing either TROP2, CDH17, or both, such that the possibility of tumor escape due to loss of tumor target antigen expression may be reduced. By binding to FAP this TriAx-I antibody also directs killing of tumor associated CAF. CAF can be a prominent cell type in the tumor microenvironment that supports tumor growth by promoting extracellular matrix remodeling, angiogenesis and immune suppression.

h8h10B2D5Tj (SEQ ID NO: 14 and 16) is an example of a penta-specific TriAx-J antibodies comprising binding specificities to DR5, in addition to TROP2, CDH17, FAP, DR5 and CD3 as in the TriAx-I antibody, h8h10B2Ti. DR5, also known as death receptor 5, TRAIL receptor 2, and tumor necrosis factor receptor superfamily member 10B, is a cell surface receptor of the TNF-receptor superfamily that binds TRAIL and mediates apoptosis. In this context, h8h10B2D5Tj antibody gains the functions of h8h10B2Ti and exerts an added ability to induce tumor cell apoptosis by engaging DR5 signaling of GI cancer cells.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this application. For example, while the above examples may include binding domains at certain positions, they are provided by way of comparison only and not by way of limitation. As such, the illustrative embodiments of the present application are not intended to be limited to the particular embodiments disclosed. Rather, they include all modifications and alternatives falling within the scope of the disclosure. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

TABLE 1

TriAx platform antibodies and their SEQ ID NO.

| TriAx Platform | Name of Antibody | Specificity (Valency) | Structural Features of LC and HC Monomers (from N- to C-Terminus) | SEQ ID NO |
|---|---|---|---|---|
| TriAx-A | h10Ta | CDH17 × CD3 | LC: L4, G1(LL)G4G1, hole | 1 |
| Bi-specific | | (1:1) | HC: h10v2, U1, G1(LL)G4G1, knob | 2 |
| | h5Ta | CDH17 × CD3 | LC: L4, G1(LL)G4G1, hole | 1 |
| | | (1:1) | HC: h5v7, U1, G1(AA)G4G1, knob | 3 |
| | h8Ta | TROP2 × CD3 | LC: L4, G1(LL)G4G1, hole | 1 |
| | | (1:1) | HC: h8v4, U1, G1(LL)G4G1, knob | 4 |
| | hB2Ta | FAP × CD3 | LC: L4, G1(FL)G4, hole | 5 |
| | | (1:1) | HC: hB2, U1, G1(FL)G4, knob | 6 |
| TriAx-C | h10C3dTc | CDH17 × CD3 × CR3 | LC: L4, G1(AA)G4G1, hole, C3d | 7 |
| Tri-specific | | (1:1:1) | HC: h10v2, U1, G1(AA)G4G1, knob | 8 |
| TriAx-D | h8C3dTd | TROP2 × CR3 | LC: h8vk, G1(LL)G4G1, hole, C3d | 9 |
| Tri-specific | | (1:2) | HC: h8vh, G1(LL)G4G1, knob, C3d | 10 |
| TriAx-E | h10Te | CDH17 × CD3 | LC: h10v2, L4, G1(LL)G4G1, hole | 11 |
| Tri-specific | | (2:1) | HC: h10v2, U1, G1(LL)G4G1, knob | 2 |
| | h8Te | TROP2 × CD3 | LC: h8v4, L4, G1(LL)G4G1, hole | 12 |
| | | (2:1) | HC: h8v4, U1, G1(LL)G4G1, knob | 4 |
| | h8h10Te | TROP2 × CDH17 × CD3 (1:1:1) | LC: h8v4, L4, G1(LL)G4G1, hole | 12 |
| | | | HC: h10v2, U1, G1(LL)G4G1, knob | 2 |
| TriAx-I | h8h10hB2Ti | TROP2 × CDH17 × CD3 × FAP | LC: h8scFv, L4, G1(LL)G4G1, hole, | 14 |
| Tetra-specific | | (1:1:1:1) | hB5scFv | |
| | | | HC: h10scFv, U1, G2(LL)G4G1, knob, | 15 |
| | | | hB5scFv | |
| TriAx-J | h8h10hB2D5Tj | TROP2 × CDH17 × CD3 × FAP × DR5 | LC: h8scFv, L4, G1(LL)G4G1, hole | 14 |
| Penta-specific | | (1:1:1:1:1) | HC: h10scFv, U1, G2(LL)G4G1, knob, | 16 |
| | | | DR5 | |

SEQUENCE LISTING

>Sequence ID NO: 1: LC Monomer for h10Ta, h5Ta, h8Ta, and hA12Ta
MRLPAQLLGLLMLWVSGSSGDIQMTQSPSSLSASVGDRVTITCQASQDISNYLNWYQQKPGKAP
KLLIYYTSRLESGVPSRFSGSGSGTDYTLTISSLQPEDFATYYCQQGNTLPWTFGQGTKVEIKG
APGGGTHTCPPCPAPELLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPRE
PQVYTLPPSREEMTKNQVSLSCAVKGFYPSDIAVEWESNGQPENNYKTTPPVLDSDGSFFLVSK
LTVDKSRWQQGNVFSCSVMHEALHNHYTQKSLSLSPGK >Sequence ID NO: 2: HC Monomer for h10Ta, h8h10Te, and h10Te
MEFGLSWVFLVALLRGVQCEVQLLESGGGLVQPGGSLRLSCAASGFTFSSYAMSWVRQAPGKGL
EWVAVIDSNGGSTYYPDTVKDRFTISRDNSKNTLYLQMNSLRAEDTAVYYCSSYTNLGAYWGQG
TLVTVSAGGGGSGGGGSGGGGSDIQMTQSPSSLSASVGDRVTITCRASQDISGYLNWLQQKPGK
AIKRLIYTTSTLDSGVPSRFSGSGSGTDFTLTISSLQPEDFATYYCLQYASSPFTFGGGTKVEI
KPAGGGGGSEVQLVESGGGLVQPGGSLRLSCAASGYSFTGYTMNWVRQAPGKGLEWVALINPYK
GVSTYNQKFKDRFTISVDKSKNTAYLQMNSLRAEDTAVYYCARSGYYGDSDWYFDVWGQGTLVT
VSSGAPGGGTHTCPPCPAPELLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKG
QPREPQVYTLPPSREEMTKNQVSLWCLVKGFYPSDIAVEWESNGQPENNYKTTPPVLDSDGSFF
LYSKLTVDKSRWQQGNVFSCSVMHEALHNHYTQKSLSLSPGK >Sequence ID NO: 3: HC Monomer for h5Ta
MAVLGLLFCLVTFPSCVLSQVQLVQSGAEVKKPGATVKISCKVSAYAFSSSWMNWVQQAPGKGL
EWIGRIYPRDGDTNYNGKFKGRVTLTADTSTDTAYMELSSLRSEDTAVYFCAREGDGYYWYFDV
WGQGTMVTVSSGGGGSGGGGSGGGGSDIVLTQSPASLAVSLGQRATISCRASQSIRNYLHWYQQ
KPGQPPKLLIKYASQSISGIPSRFSGSGSGTDFTLNIHPVEEEDAATYYCQHSNSWPLTFGAGT
KLELKPAGGGGGSEVQLVESGGGLVQPGGSLRLSCAASGYSFTGYTMNWVRQAPGKGLEWVALI
NPYKGVSTYNQKFKDRFTISVDKSKNTAYLQMNSLRAEDTAVYYCARSGYYGDSDWYFDVWGQG
TLVTVSSGAPGGGTHTCPPCPAPEAAGGPSVFLFPPKPKDTLMISRTPEVTCVVVDVSQEDPEV
QFNWYVDGVEVHNAKTKPREEQFNSTYRVVSVLTVLHQDWLNGKEYKCKVSNKGLPSSIEKTIS
KAKGQPREPQVYTLPPSREEMTKNQVSLWCLVKGFYPSDIAVEWESNGQPENNYKTTPPVLDSD
GSFFLYSKLTVDKSRWQQGNVFSCSVMHEALHNHYTQKSLSLSPGK >Sequence ID NO: 4: HC Monomer for h8Ta, and h8Te
MRLPAQLLGLLMLWVSGSSGDIQMTQSPSSLSASVGDRVTITCRASENIDNYLAWYQQKPGKVP
KLLIYAATNLADGVPSRFSGSGSGTDFTLTISSLQPEDVATYYCQHYYSNQLTFGQGTKLEIKG
GGGSGGGGSGGGGSEVQLVESGGGLVQPGGSLRLSCAASGFTFSTYTMSWVRQAPGKGLEWVAN
INSDGYNIYYSDSVKGRFTISRDNAKNSLYLQMNSLRAEDTAVYYCVRCSYYSYDYFDYWGQGT
LVTVSSPAGGGGGSEVQLVESGGGLVQPGGSLRLSCAASGYSFTGYTMNWVRQAPGKGLEWVAL
INPYKGVSTYNQKFKDRFTISVDKSKNTAYLQMNSLRAEDTAVYYCARSGYYGDSDWYFDVWGQ
GTLVTVSSGAPGGGTHTCPPCPAPELLGGPSVFLFPPKPKDTLMISRTPEVTCVVVDVSQEDPE
VQFNWYVDGVEVHNAKTKPREEQFNSTYRVVSVLTVLHQDWLNGKEYKCKVSNKGLPSSIEKTI
SKAKGQPREPQVYTLPPSREEMTKNQVSLWCLVKGFYPSDIAVEWESNGQPENNYKTTPPVLDS
DGSFFLYSKLTVDKSRWQQGNVFSCSVMHEALHNHYTQKSLSLSPGK >Sequence ID NO: 5: LC Monomer for hB2Ta
MEFGLSWVFLVALLRGVQCQVQLVQSGAEVKKPGASVKVSCKASGYSFTDYTMNWVRQAPGQGL
EWMGVINPNHGISSYAQKFQGRVTMTRDTSTSTVYMELSSLRSEDTAVYYCVRRKISYDYDEGY
AMDYWGQGTLVTVSSGGGGSGGGGSGGGGSDIVMTQSPDSLAVSLGERATINCKSSQNLLNSSN
QKNYLAWYQQKPGQPPKLLVFFAATRESGVPDRFSGSGSGTDETLTISSLQAEDVAVYYCQQHY
STPWTFGGGTKLEIKPAGGGGSEVQLVESGGGLVQPGGSLRLSCAASGYSFTGYTMNWVRQAPG
KGLEWVALINPYKGVSTYNQKFKDRFTISVDKSKNTAYLQMNSLRAEDTAVYYCARSGYYGDSD
WYFDVWGQGTLVTVSSGAPGGGTHTCPPCPAPELLGGPSVFLFPPKPKDTLMISRTPEVTCVVV
DVSQEDPEVQFNWYVDGVEVHNAKTKPREEQFNSTYRVVSVLTVLHQDWLNGKEYKCKVSNKGL
PSSIEKTISKAKGQPREPQVYTLPPSREEMTKNQVSLWCLVKGFYPSDIAVEWESNGQPENNYK
TTPPVLDSDGSFFLYSKLTVDKSRWQQGNVFSCSVMHEALHNHYTQKSLSLSPGK >Sequence ID NO: 6: HC Monomer for hB2Ta, and hA12Ta
MEFGLSWVFLVALLRGVQCEVQLVQSGAEVKKPGATVKISCKVSGFKIQDAYIHWVQQAPGKGL
EWMGRIDPANGNSKYDPKFQGRVTITADTSTDTAYMELSSLRSEDTAVYYCTRALDGYYVGMDY
WGQGTLVTVSSGGGGSGGGGSGGGGSEIVLTQSPATLSLSPGERATLSCSASSNVNYMYWYQQK
PGQAPRLLIYDTSNLASGIPARFSGSGSGTDFTLTISSLEPEDFAVYYCQQWSSNPYTFGQGTK
LEIKPAGGGGSQVQLVQSGAEVKKPGASVKVSCKASGYSFTDYTMNWVRQAPGQGLEWMGVINP
NHGISSYAQKFQGRVTMTRDTSTSTVYMELSSLRSEDTAVYYCVRRKISYDYDEGYAMDYWGQG
TLVTVSSGAPGGGTHTCPPCPAPELLGGPSVFLFPPKPKDTLMISRTPEVTCVVVDVSQEDPEV
QFNWYVDGVEVHNAKTKPREEQFNSTYRVVSVLTVLHQDWLNGKEYKCKVSNKGLPSSIEKTIS
KAKGQPREPQVYTLPPSREEMTKNQVSLWCLVKGFYPSDIAVEWESNGQPENNYKTTPPVLDSD
GSFFLYSKLTVDKSRWQQGNVFSCSVMHEALHNHYTQKSLSLSPGK >Sequence ID NO: 7: LC Monomer for hC3dh10Tc
MRLPAQLLGLLMLWVSGSSGDIQMTQSPSSLSASVGDRVTITCQASQDISNYLNWYQQKPGKAP
KLLIYYTSRLESGVPSRFSGSGSGTDYTLTISSLQPEDFATYYCQQGNTLPWTFGQGTKVEIKG
APGGGTHTCPPCPAPELLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPRE
PQVYTLPPSREEMTKNQVSLSCAVKGFYPSDIAVEWESNGQPENNYKTTPPVLDSDGSFFLVSK
LTVDKSRWQQGNVFSCSVMHEALHNHYTQKSLSLSPGKPAGGGGVDAERLKHLIVTPSGAGEQN
MIGMTPTVIAVHYLDETEQWEKFGLEKRQGALELIKKGYTQQLAFRQPSSAFAAFVKRAPSTWL
TAYVVKVFSLAVNLIAIDSQVLCGAVKWLILEKQKPDGVFQEDAPVIHQEMIGGLRNNNEKDMA -continued

SEQUENCE LISTING

LTAFVLISLQEAKDICEEQVNSLPGSITKAGDFLEANYMNLQRSYTVAIAGYALAQMGRLKGPL
LNKFLTTAKDKNRWEDPGKQLYNVEATSYALLALLQLKDFDFVPPVVRWLNEQRYYGGGYGSTQ
ATFMVFQALAQYQKDAP

>Sequence ID NO: 8: HC Monomer for hC3dh10Tc
MEFGLSWVFLVALLRGVQCEVQLLESGGGLVQPGGSLRLSCAASGFTFSSYAMSWVRQAPGKGL
EWVAVIDSNGGSTYYPDTVKDRFTISRDNSKNTLYLQMNSLRAEDTAVYYCSSYTNLGAYWGQG
TLVTVSAGGGGSGGGGSGGGGSDIQMTQSPSSLSASVGDRVTITCRASQDISGYLNWLQQKPGK
AIKRLIYTTSTLDSGVPSRFSGSGSGTDFTLTISSLQPEDFATYYCLQYASSPFTFGGGTKVEI
KPAGGGGGSEVQLVESGGGLVQPGGSLRLSCAASGYSFTGYTMNWVRQAPGKGLEWVALINPYK
GVSTYNQKFKDRFTISVDKSKNTAYLQMNSLRAEDTAVYYCARSGYYGDSDWYFDVWGQGTLVT
VSSGAPGGGTHTCPPCPAPELLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKG
QPREPQVYTLPPSREEMTKNQVSLWCLVKGFYPSDIAVEWESNGQPENNYKTTPPVLDSDGSFF
LYSKLTVDKSRWQQGNVFSCSVMHEALHNHYTQKSLSLSPGK >Sequence ID NO: 9: LC Monomer for h8C3dTa
MRLPAQLLGLLMLWVSGSSGDIQMTQSPSSLSASVGDRVTITCRASENIDNYLAWYQQKPGKVP
KLLIYAATNLADGVPSRFSGSGSGTDFTLTISSLQPEDVATYYCQHYYSNQLTFGQGTKLEIKG
APGGGTHTCPPCPAPELLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPRE
PQVYTLPPSREEMTKNQVSLSCAVKGFYPSDIAVEWESNGQPENNYKTTPPVLDSDGSFFLVSK
LTVDKSRWQQGNVFSCSVMHEALHNHYTQKSLSLSPGKPAGGGGVDAERLKHLIVTPSGAGEQN
MIGMTPTVIAVHYLDETEQWEKFGLEKRQGALELIKKGYTQQLAFRQPSSAFAAFVKRAPSTWL
TAYVVKVFSLAVNLIAIDSQVLCGAVKWLILEKQKPDGVFQEDAPVIHQEMIGGLRNNNEKDMA
LTAFVLISLQEAKDICEEQVNSLPGSITKAGDFLEANYMNLQRSYTVAIAGYALAQMGRLKGPL
LNKFLTTAKDKNRWEDPGKQLYNVEATSYALLALLQLKDFDFVPPVVRWLNEQRYYGGGYGSTQ
ATFMVFQALAQYQKDAP >Sequence ID NO: 10: HC Monomer for h8C3dTa
MEFGLSWVFLVALLRGVQCEVQLVESGGGLVQPGGSLRLSCAASGFTFSTYTMSWVRQAPGKGL
EWVANINSDGYNIYYSDSVKGRFTISRDNAKNSLYLQMNSLRAEDTAVYYCVRCSYYSYDYFDY
WGQGTLVTVSSGAPGGGTHTCPPCPAPELLGGPSVFLFPPKPKDTLMISRTPEVTCVVVDVSQE
DPEVQFNWYVDGVEVHNAKTKPREEQFNSTYRVVSVLTVLHQDWLNGKEYKCKVSNKGLPSSIE
KTISKAKGQPREPQVYTLPPSREEMTKNQVSLWCLVKGFYPSDIAVEWESNGQPENNYKTTPPV
LDSDGSFFLYSKLTVDKSRWQQGNVFSCSVMHEALHNHYTQKSLSLSPGKPAGGGGVDAERLKH
LIVTPSGAGEQNMIGMTPTVIAVHYLDETEQWEKFGLEKRQGALELIKKGYTQQLAFRQPSSAF
AAFVKRAPSTWLTAYVVKVFSLAVNLIAIDSQVLCGAVKWLILEKQKPDGVFQEDAPVIHQEMI
GGLRNNNEKDMALTAFVLISLQEAKDICEEQVNSLPGSITKAGDFLEANYMNLQRSYTVAIAGY
ALAQMGRLKGPLLNKFLTTAKDKNRWEDPGKQLYNVEATSYALLALLQLKDFDFVPPVVRWLNE
QRYYGGGYGSTQATFMVFQALAQYQKDAP >Sequence ID NO: 11: LC Monomer for h10Te
MEFGLSWVFLVALLRGVQCEVQLLESGGGLVQPGGSLRLSCAASGFTFSSYAMSWVRQAPGKGL
EWVAVIDSNGGSTYYPDTVKDRFTISRDNSKNTLYLQMNSLRAEDTAVYYCSSYTNLGAYWGQG
TLVTVSAGGGGSGGGGSGGGGSDIQMTQSPSSLSASVGDRVTITCRASQDISGYLNWLQQKPGK
AIKRLIYTTSTLDSGVPSRFSGSGSGTDFTLTISSLQPEDFATYYCLQYASSPFTFGGGTKVEI
KPAGGGGGSDIQMTQSPSSLSASVGDRVTITCQASQDISNYLNWYQQKPGKAPKLLIYYTSRLE
SGVPSRFSGSGSGTDYTLTISSLQPEDFATYYCQQGNTLPWTFGQGTKVEIKGAPGGGTHTCPP
CPAPELLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSRE
EMTKNQVSLSCAVKGFYPSDIAVEWESNGQPENNYKTTPPVLDSDGSFFLYSKLTVDKSRWQQG
NVFSCSVMHEALHNHYTQKSLSLSPGK >Sequence ID NO: 12: HL Monomer for h8Te, and h8h10Te
MRLPAQLLGLLMLWVSGSSGDIQMTQSPSSLSASVGDRVTITCRASENIDNYLAWYQQKPGKVP
KLLIYAATNLADGVPSRFSGSGSGTDFTLTISSLQPEDVATYYCQHYYSNQLTFGQGTKLEIKG
GGGSGGGGSGGGGSEVQLVESGGGLVQPGGSLRLSCAASGFTFSTYTMSWVRQAPGKGLEWVAN
INSDGYNIYYSDSVKGRFTISRDNAKNSLYLQMNSLRAEDTAVYYCVRCSYYSYDYFDYWGQGT
LVTVSSPAGGGGGSDIQMTQSPSSLSASVGDRVTITCQASQDISNYLNWYQQKPGKAPKLLIYY
TSRLESGVPSRFSGSGSGTDYTLTISSLQPEDFATYYCQQGNTLPWTFGQGTKVEIKGAPGGGT
HTCPPCPAPELLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVYTL
PPSREEMTKNQVSLSCAVKGFYPSDIAVEWESNGQPENNYKTTPPVLDSDGSFFLVSKLTVDKS
RWQQGNVFSCSVMHEALHNHYTQKSLSLSPGK >Sequence ID NO: 13: L4, Germline CDR-L1 with R24Q and R30S
DIQMTQSPSSLSASVGDRVTITCQASQDISNYLNWYQQKPGKAPKLLIYYTSRLESGVPSRFSG
SGSGTDYTLTISSLQPEDFATYYCQQGNTLPWTFGQGTKVEIK >Sequence ID NO: 14: LC Monomer for h8h10hB2Ti, and h8h10hB2D5Ti
MRLPAQLLGLLMLWVSGSSGDIQMTQSPSSLSASVGDRVTITCRASENIDNYLAWYQQKPGKVP
KLLIYAATNLADGVPSRFSGSGSGTDFTLTISSLQPEDVATYYCQHYYSNQLTFGQGTKLEIKG
GGGSGGGGSGGGGSEVQLVESGGGLVQPGGSLRLSCAASGFTFSTYTMSWVRQAPGKGLEWVAN
INSDGYNIYYSDSVKGRFTISRDNAKNSLYLQMNSLRAEDTAVYYCVRCSYYSYDYFDYWGQGT
LVTVSSPAGGGGGSDIQMTQSPSSLSASVGDRVTITCQASQDISNYLNWYQQKPGKAPKLLIYY
TSRLESGVPSRFSGSGSGTDYTLTISSLQPEDFATYYCQQGNTLPWTFGQGTKVEIKGAPGGGT -continued

SEQUENCE LISTING

HTCPPCPAPELLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVYTL
PPSREEMTKNQVSLSCAVKGFYPSDIAVEWESNGQPENNYKTTPPVLDSDGSFFLVSKLTVDKS
RWQQGNVFSCSVMHEALHNHYTQKSLSLSPGKPGGGGSQVQLVQSGAEVKKPGASVKVSCKASG
YSFTDYTMNWVRQAPGQGLEWMGVINPNHGISSYAQKFQGRVTMTRDTSTSTVYMELSSLRSED
TAVYYCVRRKISYDYDEGYAMDYWGQGTLVTVSSGGGGSGGGGSGGGGSDIVMTQSPDSLAVSL
GERATINCKSSQNLLNSSNQKNYLAWYQQKPGQPPKLLVFFAATRESGVPDRFSGSGSGTDFTL
TISSLQAEDVAVYYCQQHYSTPWTFGGGTKLEIK

>Sequence ID NO: 15: HC Monomer for h8h10hB2Ti
MEFGLSWVFLVALLRGVQCEVQLLESGGGLVQPGGSLRLSCAASGFTFSSYAMSWVRQAPGKGL
EWVAVIDSNGGSTYYPDTVKDRFTISRDNSKNTLYLQMNSLRAEDTAVYYCSSYTNLGAYWGQG
TLVTVSAGGGGSGGGGSGGGGSDIQMTQSPSSLSASVGDRVTITCRASQDISGYLNWLQQKPGK
AIKRLIYTTSTLDSGVPSRFSGSGSGTDFTLTISSLQPEDFATYYCLQYASSPFTFGGGTKVEI
KPAGGGGGSEVQLVESGGGLVQPGGSLRLSCAASGYSFTGYTMNWVRQAPGKGLEWVALINPYK
GVSTYNQKFKDRFTISVDKSKNTAYLQMNSLRAEDTAVYYCARSGYYGDSDWYFDVWGQGTLVT
VSSGAPGGGTHTCPPCPAPELLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKG
QPREPQVYTLPPSREEMTKNQVSLWCLVKGFYPSDIAVEWESNGQPENNYKTTPPVLDSDGSFF
LYSKLTVDKSRWQQGNVFSCSVMHEALHNHYTQKSLSLSPGK >Sequence ID NO: 16: HC Monomer for h8h10hB2D5Ti
MEFGLSWVFLVALLRGVQCEVQLLESGGGLVQPGGSLRLSCAASGFTFSSYAMSWVRQAPGKGL
EWVAVIDSNGGSTYYPDTVKDRFTISRDNSKNTLYLQMNSLRAEDTAVYYCSSYTNLGAYWGQG
TLVTVSAGGGGSGGGGSGGGGSDIQMTQSPSSLSASVGDRVTITCRASQDISGYLNWLQQKPGK
AIKRLIYTTSTLDSGVPSRFSGSGSGTDFTLTISSLQPEDFATYYCLQYASSPFTFGGGTKVEI
KPAGGGGGSEVQLVESGGGLVQPGGSLRLSCAASGYSFTGYTMNWVRQAPGKGLEWVALINPYK
GVSTYNQKFKDRFTISVDKSKNTAYLQMNSLRAEDTAVYYCARSGYYGDSDWYFDVWGQGTLVT
VSSGAPGGGTHTCPPCPAPELLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKG
QPREPQVYTLPPSREEMTKNQVSLWCLVKGFYPSDIAVEWESNGQPENNYKTTPPVLDSDGSFF
LYSKLTVDKSRWQQGNVFSCSVMHEALHNHYTQKSLSLSPGKPGGGGSEVQLVQSGGGVERPGG
SLRLSCAASGFTFDDYGMSWVRQAPGKGLEWVSGINWNGGSTGYADSVKGRVTISRDNAKNSLY
LQMNSLRAEDTAVYYCAKILGAGRGWYFDLWGKGTTVTVSGGGGSGGGGSGGGGSSSELTQDPA
VSVALGQTVRITCQGDSLRSYYASWYQQKPGQAPVLVIYGKNNRPSGIPDRFSGSSSGNTASLT
ITGAQAEDEADYYCNSRDSSGNHVVFGGGTKLTVL >Sequence ID NO: 17:
RASQDIRNY >Sequence ID NO: 18:
PAGGGGS >Sequence ID NO: 19:
PAGPPA >Sequence ID NO: 20:
PAGPAP >Sequence ID NO: 21:
PAGPPP >Sequence ID NO: 22:
GAPGGGG

What is claimed is:

1. A multi-specific antibody having a N-terminus and a C-terminus, comprising a first monomer, comprising from the N-terminus to the C-terminus, a VL domain, first linker, and a first Fc domain, a second monomer, comprising from the N-terminus to the C-terminus, a VH domain, a second linker, and a second Fc domain, and at least a first binding domain linked to either the N-terminus or the C-terminus of the first monomer or the second monomer, wherein the first monomer and the second monomer are paired through the interaction between the VL domain and the VH domain, and wherein the multi-specific antibody is stabilized by a disulfide bond between the first linker and the second linker, and wherein the first monomer comprises the amino acid sequence of SEQ ID NO: 1 and the second monomer comprises the amino acid sequence of SEQ ID NO: 2, 3, or 4, the first monomer comprises the amino acid sequence of SEQ ID NO: 5 and the second monomer comprises the amino acid sequence of SEQ ID NO: 6, the first monomer comprises the amino acid sequence of SEQ ID NO: 7 and the second monomer comprises the amino acid sequence of SEQ ID NO: 8, the first monomer comprises the amino acid sequence of SEQ ID NO: 9 and the second monomer comprises the amino acid sequence of SEQ ID NO: 10 the first monomer comprises the amino acid sequence of SEQ ID NO: 11 and the second monomer comprises the amino acid sequence of SEQ ID NO: 2, or the first monomer comprises the amino acid sequence of SEQ ID NO: 12 and the second monomer comprises the amino acid sequence of SEQ ID NO: 4 or 2.

2. The multi-specific antibody of claim 1, wherein the first binding domain is linked to the VH domain at the N-terminus, or the VL domain at the N-terminus.

3. The multi-specific antibody of claim 1, further comprising at least a second binding domain, wherein the first binding domain and the second binding domain are linked to the opposite termini of the multi-specific antibody.

4. The multi-specific antibody of claim 1, further comprising a second binding domain, wherein the first binding domain and the second binding domain are linked to the same terminus of the multi-specific antibody, and wherein the first binding domain and the second binding domain are independently selected from a scFv, a ligand, a single domain antibody, the binding region of a natural protein, a chemokine and a cytokine.

5. The multi-specific antibody of claim 1, further comprising a second binding domain, wherein the first binding domain is linked to the N-terminus of the VH domain and the second binding domain is linked to the N-terminus of the VL domain, or wherein the first binding domain is linked to the C-terminus of the first Fc domain and the second binding domain is linked to the C-terminus of the second Fc domain.

6. The multi-specific antibody of claim 1, further comprising a second binding domain, wherein the first binding domain is linked to the N-terminus of the VH domain and the second binding domain is linked to the N-terminus of the VL domain, and a third binding domain, wherein the third binding domain is linked to the C-terminus of the first Fc domain or the C-terminus of the second Fc domain.

7. The multi-specific antibody of claim 1, further comprising a second binding domain, wherein the first binding domain is linked to the N-terminus of the VH domain and the second binding domain is linked to the N-terminus of the VL domain, a third binding domain and a fourth binding domain, wherein the third binding domain is linked to the C-terminus of the first Fc domain and the fourth binding domain is linked to the C-terminus of the second Fc domain, wherein the first, second, third, and fourth binding domains are independently selected from a scFv, a ligand, a single domain antibody, the binding region of a natural protein, a chemokine and a cytokine.

8. The multi-specific antibody of claim 7, wherein the first, second and third binding domains are different from each other and wherein the fourth binding domain is the same to one of the first, second and third binding domains.

9. The multi-specific antibody of claim 1, further comprising a second binding domain, wherein the first binding domain is linked to the C-terminus of the first Fc domain and the second binding domain is linked to the C-terminus of the second Fc domain, wherein the first and second binding domains are independently selected from a scFv, a ligand, a single domain antibody, the binding region of a natural protein, a chemokine and a cytokine.

10. The multi-specific antibody of claim 1, further comprising a second binding domain, wherein the first binding domain is linked to the N-terminus of the VH domain and the second binding domain is linked to the C-terminus of the first Fc domain.

11. The multi-specific antibody of claim 1, wherein the first binding domain comprise a scFv, a ligand, a single domain antibody, the binding region of a natural protein, a chemokine or a cytokine.

12. The multi-specific antibody of claim 1, wherein the first monomer comprises the amino acid sequence of SEQ ID NO: 1 and the second monomer comprises the amino acid sequence of SEQ ID NO: 2, 3, or 4, or wherein the first monomer comprises amino acid sequence of SEQ ID NO: 5 and the second monomer comprises the amino acid sequence of SEQ ID NO: 6.

13. The multi-specific antibody of claim 1, wherein the first monomer comprises the amino acid sequence of SEQ ID NO: 7 and wherein the second monomer comprises the amino acid sequence of SEQ ID NO: 8 the first monomer comprises the amino acid sequence of SEQ ID NO: 9 and the second monomer comprises the amino acid sequence of SEQ ID NO: 10, the first monomer comprises the amino acid sequence of SEQ ID NO: 11 and the second monomer comprises the amino acid sequence of SEQ ID NO: 2, or the first monomer comprises the amino acid sequence of SEQ ID NO: 12 and the second monomer comprises the amino acid sequence of SEQ ID NO: 4 or 2.

14. An immunoconjugate comprising the multi-specific antibody of claim 1, and a cytotoxic agent or an imaging agent.

15. A pharmaceutical composition, comprising the immunoconjugate of claim 14 and a pharmaceutically acceptable carrier.

16. A pharmaceutical composition, comprising the multi-specific antibody of claim 1 and a pharmaceutically acceptable carrier.

17. The pharmaceutical composition of claim 16, further comprising a radioisotope, a radionuclide, a toxin, a therapeutic agent, a chemotherapeutic agent or a combination thereof.

* * * * *

SEQUENCE LISTING

<160> NUMBER OF SEQ ID NOS: 22

<210> SEQ ID NO 1
<211> LENGTH: 358
<212> TYPE: PRT
<213> ORGANISM: Artificial Sequence
<220> FEATURE:
<223> OTHER INFORMATION: Synthesized

<400> SEQUENCE: 1

Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
            20                  25                  30

```
Ala Ser Val Gly Asp Arg Val Thr Ile Thr Cys Gln Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Tyr Thr Ser Arg Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Asn
            100                 105                 110

Thr Leu Pro Trp Thr Phe Gly Gln Gly Thr Lys Val Glu Ile Lys Gly
        115                 120                 125

Ala Pro Gly Gly Gly Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser Gln Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Gly Leu Pro
225                 230                 235                 240

Ser Ser Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Ser Cys Ala Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Val Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355
```

<210> SEQ ID NO 2
<211> LENGTH: 618
<212> TYPE: PRT
<213> ORGANISM: Artificial Sequence
<220> FEATURE:
<223> OTHER INFORMATION: Synthesized

<400> SEQUENCE: 2

```
Met Glu Phe Gly Leu Ser Trp Val Phe Leu Val Ala Leu Leu Arg Gly
1               5                   10                  15

Val Gln Cys Glu Val Gln Leu Leu Glu Ser Gly Gly Gly Leu Val Gln
            20                  25                  30
```

-continued

```
Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ala Val Ile Asp Ser Asn Gly Gly Ser Thr Tyr Tyr Pro
65                  70                  75                  80

Asp Thr Val Lys Asp Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ser Ser Tyr Thr Asn Leu Gly Ala Tyr Trp Gly Gln Gly
        115                 120                 125

Thr Leu Val Thr Val Ser Ala Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Ser Gly Tyr Leu Asn Trp Leu Gln Gln Lys Pro Gly Lys
            180                 185                 190

Ala Ile Lys Arg Leu Ile Tyr Thr Thr Ser Thr Leu Asp Ser Gly Val
        195                 200                 205

Pro Ser Arg Phe Ser Gly Ser Gly Ser Gly Thr Asp Phe Thr Leu Thr
    210                 215                 220

Ile Ser Ser Leu Gln Pro Glu Asp Phe Ala Thr Tyr Tyr Cys Leu Gln
225                 230                 235                 240

Tyr Ala Ser Ser Pro Phe Thr Phe Gly Gly Gly Thr Lys Val Glu Ile
                245                 250                 255

Lys Pro Ala Gly Gly Gly Gly Gly Ser Glu Val Gln Leu Val Glu Ser
            260                 265                 270

Gly Gly Gly Leu Val Gln Pro Gly Gly Ser Leu Arg Leu Ser Cys Ala
        275                 280                 285

Ala Ser Gly Tyr Ser Phe Thr Gly Tyr Thr Met Asn Trp Val Arg Gln
    290                 295                 300

Ala Pro Gly Lys Gly Leu Glu Trp Val Ala Leu Ile Asn Pro Tyr Lys
305                 310                 315                 320

Gly Val Ser Thr Tyr Asn Gln Lys Phe Lys Asp Arg Phe Thr Ile Ser
                325                 330                 335

Val Asp Lys Ser Lys Asn Thr Ala Tyr Leu Gln Met Asn Ser Leu Arg
            340                 345                 350

Ala Glu Asp Thr Ala Val Tyr Tyr Cys Ala Arg Ser Gly Tyr Tyr Gly
        355                 360                 365

Asp Ser Asp Trp Tyr Phe Asp Val Trp Gly Gln Gly Thr Leu Val Thr
    370                 375                 380

Val Ser Ser Gly Ala Pro Gly Gly Gly Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser Gln Glu Asp Pro Glu Val Gln Phe Asn Trp
        435                 440                 445
```

```
Tyr Val Asp Gly Val Glu Val His Asn Ala Lys Thr Lys Pro Arg Glu
    450                 455                 460

Glu Gln Phe Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Gly Leu Pro Ser Ser Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Trp Cys Leu Val Lys Gly Phe Tyr
    530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys
    610                 615


<210> SEQ ID NO 3
<211> LENGTH: 622
<212> TYPE: PRT
<213> ORGANISM: Artificial Sequence
<220> FEATURE:
<223> OTHER INFORMATION: Synthesized

<400> SEQUENCE: 3

Met Ala Val Leu Gly Leu Leu Phe Cys Leu Val Thr Phe Pro Ser Cys
1               5                   10                  15

Val Leu Ser Gln Val Gln Leu Val Gln Ser Gly Ala Glu Val Lys Lys
            20                  25                  30

Pro Gly Ala Thr Val Lys Ile Ser Cys Lys Val Ser Ala Tyr Ala Phe
        35                  40                  45

Ser Ser Ser Trp Met Asn Trp Val Gln Gln Ala Pro Gly Lys Gly Leu
    50                  55                  60

Glu Trp Ile Gly Arg Ile Tyr Pro Arg Asp Gly Asp Thr Asn Tyr Asn
65                  70                  75                  80

Gly Lys Phe Lys Gly Arg Val Thr Leu Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Phe Cys Ala Arg Glu Gly Asp Gly Tyr Tyr Trp Tyr Phe Asp Val
        115                 120                 125

Trp Gly Gln Gly Thr Met Val Thr Val Ser Ser Gly Gly Gly Gly Ser
    130                 135                 140

Gly Gly Gly Gly Ser Gly Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Gln Ser Ile Arg Asn Tyr Leu His Trp Tyr Gln Gln
            180                 185                 190
```

```
Lys Pro Gly Gln Pro Pro Lys Leu Leu Ile Lys Tyr Ala Ser Gln Ser
        195                 200                 205

Ile Ser Gly Ile Pro Ser Arg Phe Ser Gly Ser Gly Ser Gly Thr Asp
    210                 215                 220

Phe Thr Leu Asn Ile His Pro Val Glu Glu Glu Asp Ala Ala Thr Tyr
225                 230                 235                 240

Tyr Cys Gln His Ser Asn Ser Trp Pro Leu Thr Phe Gly Ala Gly Thr
                245                 250                 255

Lys Leu Glu Leu Lys Pro Ala Gly Gly Gly Gly Gly Ser Glu Val Gln
            260                 265                 270

Leu Val Glu Ser Gly Gly Gly Leu Val Gln Pro Gly Gly Ser Leu Arg
        275                 280                 285

Leu Ser Cys Ala Ala Ser Gly Tyr Ser Phe Thr Gly Tyr Thr Met Asn
    290                 295                 300

Trp Val Arg Gln Ala Pro Gly Lys Gly Leu Glu Trp Val Ala Leu Ile
305                 310                 315                 320

Asn Pro Tyr Lys Gly Val Ser Thr Tyr Asn Gln Lys Phe Lys Asp Arg
                325                 330                 335

Phe Thr Ile Ser Val Asp Lys Ser Lys Asn Thr Ala Tyr Leu Gln Met
            340                 345                 350

Asn Ser Leu Arg Ala Glu Asp Thr Ala Val Tyr Tyr Cys Ala Arg Ser
        355                 360                 365

Gly Tyr Tyr Gly Asp Ser Asp Trp Tyr Phe Asp Val Trp Gly Gln Gly
    370                 375                 380

Thr Leu Val Thr Val Ser Ser Gly Ala Pro Gly Gly Gly Thr His Thr
385                 390                 395                 400

Cys Pro Pro Cys Pro Ala Pro Glu Ala Ala Gly Gly Pro Ser Val Phe
                405                 410                 415

Leu Phe Pro Pro Lys Pro Lys Asp Thr Leu Met Ile Ser Arg Thr Pro
            420                 425                 430

Glu Val Thr Cys Val Val Val Asp Val Ser Gln Glu Asp Pro Glu Val
        435                 440                 445

Gln Phe Asn Trp Tyr Val Asp Gly Val Glu Val His Asn Ala Lys Thr
    450                 455                 460

Lys Pro Arg Glu Glu Gln Phe Asn Ser Thr Tyr Arg Val Val Ser Val
465                 470                 475                 480

Leu Thr Val Leu His Gln Asp Trp Leu Asn Gly Lys Glu Tyr Lys Cys
                485                 490                 495

Lys Val Ser Asn Lys Gly Leu Pro Ser Ser Ile Glu Lys Thr Ile Ser
            500                 505                 510

Lys Ala Lys Gly Gln Pro Arg Glu Pro Gln Val Tyr Thr Leu Pro Pro
        515                 520                 525

Ser Arg Glu Glu Met Thr Lys Asn Gln Val Ser Leu Trp Cys Leu Val
    530                 535                 540

Lys Gly Phe Tyr Pro Ser Asp Ile Ala Val Glu Trp Glu Ser Asn Gly
545                 550                 555                 560

Gln Pro Glu Asn Asn Tyr Lys Thr Thr Pro Pro Val Leu Asp Ser Asp
                565                 570                 575

Gly Ser Phe Phe Leu Tyr Ser Lys Leu Thr Val Asp Lys Ser Arg Trp
            580                 585                 590

Gln Gln Gly Asn Val Phe Ser Cys Ser Val Met His Glu Ala Leu His
        595                 600                 605

Asn His Tyr Thr Gln Lys Ser Leu Ser Leu Ser Pro Gly Lys
```

610 615 620

<210> SEQ ID NO 4
<211> LENGTH: 623
<212> TYPE: PRT
<213> ORGANISM: Artificial Sequence
<220> FEATURE:
<223> OTHER INFORMATION: Synthesized

<400> SEQUENCE: 4

Met Arg Leu Pro Ala Gln Leu Leu Gly Leu Leu Met Leu Trp Val Ser
1 5 10 15

Gly Ser Ser Gly Asp Ile Gln Met Thr Gln Ser Pro Ser Ser Leu Ser
20 25 30

Ala Ser Val Gly Asp Arg Val Thr Ile Thr Cys Arg Ala Ser Glu Asn
35 40 45

Ile Asp Asn Tyr Leu Ala Trp Tyr Gln Gln Lys Pro Gly Lys Val Pro
50 55 60

Lys Leu Leu Ile Tyr Ala Ala Thr Asn Leu Ala Asp Gly Val Pro Ser
65 70 75 80

Arg Phe Ser Gly Ser Gly Ser Gly Thr Asp Phe Thr Leu Thr Ile Ser
85 90 95

Ser Leu Gln Pro Glu Asp Val Ala Thr Tyr Tyr Cys Gln His Tyr Tyr
100 105 110

Ser Asn Gln Leu Thr Phe Gly Gln Gly Thr Lys Leu Glu Ile Lys Gly
115 120 125

Gly Gly Gly Ser Gly Gly Gly Gly Ser Gly Gly Gly Gly Ser Glu Val
130 135 140

Gln Leu Val Glu Ser Gly Gly Gly Leu Val Gln Pro Gly Gly Ser Leu
145 150 155 160

Arg Leu Ser Cys Ala Ala Ser Gly Phe Thr Phe Ser Thr Tyr Thr Met
165 170 175

Ser Trp Val Arg Gln Ala Pro Gly Lys Gly Leu Glu Trp Val Ala Asn
180 185 190

Ile Asn Ser Asp Gly Tyr Asn Ile Tyr Tyr Ser Asp Ser Val Lys Gly
195 200 205

Arg Phe Thr Ile Ser Arg Asp Asn Ala Lys Asn Ser Leu Tyr Leu Gln
210 215 220

Met Asn Ser Leu Arg Ala Glu Asp Thr Ala Val Tyr Tyr Cys Val Arg
225 230 235 240

Cys Ser Tyr Tyr Ser Tyr Asp Tyr Phe Asp Tyr Trp Gly Gln Gly Thr
245 250 255

Leu Val Thr Val Ser Ser Pro Ala Gly Gly Gly Gly Gly Ser Glu Val
260 265 270

Gln Leu Val Glu Ser Gly Gly Gly Leu Val Gln Pro Gly Gly Ser Leu
275 280 285

Arg Leu Ser Cys Ala Ala Ser Gly Tyr Ser Phe Thr Gly Tyr Thr Met
290 295 300

Asn Trp Val Arg Gln Ala Pro Gly Lys Gly Leu Glu Trp Val Ala Leu
305 310 315 320

Ile Asn Pro Tyr Lys Gly Val Ser Thr Tyr Asn Gln Lys Phe Lys Asp
325 330 335

Arg Phe Thr Ile Ser Val Asp Lys Ser Lys Asn Thr Ala Tyr Leu Gln
340 345 350

Met Asn Ser Leu Arg Ala Glu Asp Thr Ala Val Tyr Tyr Cys Ala Arg

```
        355                 360                 365

Ser Gly Tyr Tyr Gly Asp Ser Asp Trp Tyr Phe Asp Val Trp Gly Gln
    370                 375                 380

Gly Thr Leu Val Thr Val Ser Ser Gly Ala Pro Gly Gly Gly Thr His
385                 390                 395                 400

Thr Cys Pro Pro Cys Pro Ala Pro Glu Leu Leu Gly Gly Pro Ser Val
                405                 410                 415

Phe Leu Phe Pro Pro Lys Pro Lys Asp Thr Leu Met Ile Ser Arg Thr
            420                 425                 430

Pro Glu Val Thr Cys Val Val Val Asp Val Ser Gln Glu Asp Pro Glu
        435                 440                 445

Val Gln Phe Asn Trp Tyr Val Asp Gly Val Glu Val His Asn Ala Lys
    450                 455                 460

Thr Lys Pro Arg Glu Glu Gln Phe Asn Ser Thr Tyr Arg Val Val Ser
465                 470                 475                 480

Val Leu Thr Val Leu His Gln Asp Trp Leu Asn Gly Lys Glu Tyr Lys
                485                 490                 495

Cys Lys Val Ser Asn Lys Gly Leu Pro Ser Ser Ile Glu Lys Thr Ile
            500                 505                 510

Ser Lys Ala Lys Gly Gln Pro Arg Glu Pro Gln Val Tyr Thr Leu Pro
        515                 520                 525

Pro Ser Arg Glu Glu Met Thr Lys Asn Gln Val Ser Leu Trp Cys Leu
    530                 535                 540

Val Lys Gly Phe Tyr Pro Ser Asp Ile Ala Val Glu Trp Glu Ser Asn
545                 550                 555                 560

Gly Gln Pro Glu Asn Asn Tyr Lys Thr Thr Pro Pro Val Leu Asp Ser
                565                 570                 575

Asp Gly Ser Phe Phe Leu Tyr Ser Lys Leu Thr Val Asp Lys Ser Arg
            580                 585                 590

Trp Gln Gln Gly Asn Val Phe Ser Cys Ser Val Met His Glu Ala Leu
        595                 600                 605

His Asn His Tyr Thr Gln Lys Ser Leu Ser Leu Ser Pro Gly Lys
    610                 615                 620


<210> SEQ ID NO 5
<211> LENGTH: 631
<212> TYPE: PRT
<213> ORGANISM: Artificial Sequence
<220> FEATURE:
<223> OTHER INFORMATION: Synthesized

<400> SEQUENCE: 5

Met Glu Phe Gly Leu Ser Trp Val Phe Leu Val Ala Leu Leu Arg Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Asp Tyr Thr Met Asn Trp Val Arg Gln Ala Pro Gly Gln Gly Leu
    50                  55                  60

Glu Trp Met Gly Val Ile Asn Pro Asn His Gly Ile Ser Ser Tyr Ala
65                  70                  75                  80

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
```

-continued

```
            100                 105                 110

Tyr Tyr Cys Val Arg Arg Lys Ile Ser Tyr Asp Tyr Asp Glu Gly Tyr
        115                 120                 125

Ala Met Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ser Pro Asp Ser Leu Ala Val Ser Leu Gly Glu Arg
                165                 170                 175

Ala Thr Ile Asn Cys Lys Ser Ser Gln Asn Leu Leu Asn Ser Ser Asn
            180                 185                 190

Gln Lys Asn Tyr Leu Ala Trp Tyr Gln Gln Lys Pro Gly Gln Pro Pro
        195                 200                 205

Lys Leu Leu Val Phe Phe Ala Ala Thr Arg Glu Ser Gly Val Pro Asp
    210                 215                 220

Arg Phe Ser Gly Ser Gly Ser Gly Thr Asp Phe Thr Leu Thr Ile Ser
225                 230                 235                 240

Ser Leu Gln Ala Glu Asp Val Ala Val Tyr Tyr Cys Gln Gln His Tyr
                245                 250                 255

Ser Thr Pro Trp Thr Phe Gly Gly Gly Thr Lys Leu Glu Ile Lys Pro
            260                 265                 270

Ala Gly Gly Gly Gly Ser Glu Val Gln Leu Val Glu Ser Gly Gly Gly
        275                 280                 285

Leu Val Gln Pro Gly Gly Ser Leu Arg Leu Ser Cys Ala Ala Ser Gly
    290                 295                 300

Tyr Ser Phe Thr Gly Tyr Thr Met Asn Trp Val Arg Gln Ala Pro Gly
305                 310                 315                 320

Lys Gly Leu Glu Trp Val Ala Leu Ile Asn Pro Tyr Lys Gly Val Ser
                325                 330                 335

Thr Tyr Asn Gln Lys Phe Lys Asp Arg Phe Thr Ile Ser Val Asp Lys
            340                 345                 350

Ser Lys Asn Thr Ala Tyr Leu Gln Met Asn Ser Leu Arg Ala Glu Asp
        355                 360                 365

Thr Ala Val Tyr Tyr Cys Ala Arg Ser Gly Tyr Tyr Gly Asp Ser Asp
    370                 375                 380

Trp Tyr Phe Asp Val Trp Gly Gln Gly Thr Leu Val Thr Val Ser Ser
385                 390                 395                 400

Gly Ala Pro Gly Gly Gly Thr His Thr Cys Pro Pro Cys Pro Ala Pro
                405                 410                 415

Glu Leu Leu Gly Gly Pro Ser Val Phe Leu Phe Pro Pro Lys Pro Lys
            420                 425                 430

Asp Thr Leu Met Ile Ser Arg Thr Pro Glu Val Thr Cys Val Val Val
        435                 440                 445

Asp Val Ser Gln Glu Asp Pro Glu Val Gln Phe Asn Trp Tyr Val Asp
    450                 455                 460

Gly Val Glu Val His Asn Ala Lys Thr Lys Pro Arg Glu Glu Gln Phe
465                 470                 475                 480

Asn Ser Thr Tyr Arg Val Val Ser Val Leu Thr Val Leu His Gln Asp
                485                 490                 495

Trp Leu Asn Gly Lys Glu Tyr Lys Cys Lys Val Ser Asn Lys Gly Leu
            500                 505                 510

Pro Ser Ser Ile Glu Lys Thr Ile Ser Lys Ala Lys Gly Gln Pro Arg
        515                 520                 525
```

```
Glu Pro Gln Val Tyr Thr Leu Pro Pro Ser Arg Glu Glu Met Thr Lys
    530                 535                 540

Asn Gln Val Ser Leu Trp Cys Leu Val Lys Gly Phe Tyr Pro Ser Asp
545                 550                 555                 560

Ile Ala Val Glu Trp Glu Ser Asn Gly Gln Pro Glu Asn Asn Tyr Lys
                565                 570                 575

Thr Thr Pro Pro Val Leu Asp Ser Asp Gly Ser Phe Phe Leu Tyr Ser
            580                 585                 590

Lys Leu Thr Val Asp Lys Ser Arg Trp Gln Gln Gly Asn Val Phe Ser
        595                 600                 605

Cys Ser Val Met His Glu Ala Leu His Asn His Tyr Thr Gln Lys Ser
    610                 615                 620

Leu Ser Leu Ser Pro Gly Lys
625                 630


<210> SEQ ID NO 6
<211> LENGTH: 622
<212> TYPE: PRT
<213> ORGANISM: Artificial Sequence
<220> FEATURE:
<223> OTHER INFORMATION: Synthesized

<400> SEQUENCE: 6

Met Glu Phe Gly Leu Ser Trp Val Phe Leu Val Ala Leu Leu Arg Gly
1               5                   10                  15

Val Gln Cys Glu Val Gln Leu Val Gln Ser Gly Ala Glu Val Lys Lys
            20                  25                  30

Pro Gly Ala Thr Val Lys Ile Ser Cys Lys Val Ser Gly Phe Lys Ile
        35                  40                  45

Gln Asp Ala Tyr Ile His Trp Val Gln Gln Ala Pro Gly Lys Gly Leu
    50                  55                  60

Glu Trp Met Gly Arg Ile Asp Pro Ala Asn Gly Asn Ser Lys Tyr Asp
65                  70                  75                  80

Pro Lys Phe Gln Gly Arg Val Thr Ile Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Thr Arg Ala Leu Asp Gly Tyr Tyr Val Gly Met Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Ser Ala Ser Ser Asn Val Asn Tyr Met Tyr Trp Tyr Gln Gln Lys
            180                 185                 190

Pro Gly Gln Ala Pro Arg Leu Leu Ile Tyr Asp Thr Ser Asn Leu Ala
        195                 200                 205

Ser Gly Ile Pro Ala Arg Phe Ser Gly Ser Gly Ser Gly Thr Asp Phe
    210                 215                 220

Thr Leu Thr Ile Ser Ser Leu Glu Pro Glu Asp Phe Ala Val Tyr Tyr
225                 230                 235                 240

Cys Gln Gln Trp Ser Ser Asn Pro Tyr Thr Phe Gly Gln Gly Thr Lys
                245                 250                 255
```

```
Leu Glu Ile Lys Pro Ala Gly Gly Gly Gly Ser Gln Val Gln Leu Val
            260                 265                 270

Gln Ser Gly Ala Glu Val Lys Lys Pro Gly Ala Ser Val Lys Val Ser
        275                 280                 285

Cys Lys Ala Ser Gly Tyr Ser Phe Thr Asp Tyr Thr Met Asn Trp Val
    290                 295                 300

Arg Gln Ala Pro Gly Gln Gly Leu Glu Trp Met Gly Val Ile Asn Pro
305                 310                 315                 320

Asn His Gly Ile Ser Ser Tyr Ala Gln Lys Phe Gln Gly Arg Val Thr
                325                 330                 335

Met Thr Arg Asp Thr Ser Thr Ser Thr Val Tyr Met Glu Leu Ser Ser
            340                 345                 350

Leu Arg Ser Glu Asp Thr Ala Val Tyr Tyr Cys Val Arg Arg Lys Ile
        355                 360                 365

Ser Tyr Asp Tyr Asp Glu Gly Tyr Ala Met Asp Tyr Trp Gly Gln Gly
    370                 375                 380

Thr Leu Val Thr Val Ser Ser Gly Ala Pro Gly Gly Gly Thr His Thr
385                 390                 395                 400

Cys Pro Pro Cys Pro Ala Pro Glu Leu Leu Gly Gly Pro Ser Val Phe
                405                 410                 415

Leu Phe Pro Pro Lys Pro Lys Asp Thr Leu Met Ile Ser Arg Thr Pro
            420                 425                 430

Glu Val Thr Cys Val Val Val Asp Val Ser Gln Glu Asp Pro Glu Val
        435                 440                 445

Gln Phe Asn Trp Tyr Val Asp Gly Val Glu Val His Asn Ala Lys Thr
    450                 455                 460

Lys Pro Arg Glu Glu Gln Phe Asn Ser Thr Tyr Arg Val Val Ser Val
465                 470                 475                 480

Leu Thr Val Leu His Gln Asp Trp Leu Asn Gly Lys Glu Tyr Lys Cys
                485                 490                 495

Lys Val Ser Asn Lys Gly Leu Pro Ser Ser Ile Glu Lys Thr Ile Ser
            500                 505                 510

Lys Ala Lys Gly Gln Pro Arg Glu Pro Gln Val Tyr Thr Leu Pro Pro
        515                 520                 525

Ser Arg Glu Glu Met Thr Lys Asn Gln Val Ser Leu Trp Cys Leu Val
    530                 535                 540

Lys Gly Phe Tyr Pro Ser Asp Ile Ala Val Glu Trp Glu Ser Asn Gly
545                 550                 555                 560

Gln Pro Glu Asn Asn Tyr Lys Thr Thr Pro Pro Val Leu Asp Ser Asp
                565                 570                 575

Gly Ser Phe Phe Leu Tyr Ser Lys Leu Thr Val Asp Lys Ser Arg Trp
            580                 585                 590

Gln Gln Gly Asn Val Phe Ser Cys Ser Val Met His Glu Ala Leu His
        595                 600                 605

Asn His Tyr Thr Gln Lys Ser Leu Ser Leu Ser Pro Gly Lys
    610                 615                 620
```

<210> SEQ ID NO 7
<211> LENGTH: 657
<212> TYPE: PRT
<213> ORGANISM: Artificial Sequence
<220> FEATURE:
<223> OTHER INFORMATION: Synthesized

<400> SEQUENCE: 7

-continued

```
Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Tyr Thr Ser Arg Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Asn
            100                 105                 110

Thr Leu Pro Trp Thr Phe Gly Gln Gly Thr Lys Val Glu Ile Lys Gly
        115                 120                 125

Ala Pro Gly Gly Gly Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser Gln Glu Asp Pro Glu Val Gln Phe Asn Trp Tyr Val Asp Gly
            180                 185                 190

Val Glu Val His Asn Ala Lys Thr Lys Pro Arg Glu Glu Gln Phe Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Gly Leu Pro
225                 230                 235                 240

Ser Ser Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Ser Cys Ala Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Val Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys Pro Ala Gly Gly Gly Gly Val Asp Ala Glu
        355                 360                 365

Arg Leu Lys His Leu Ile Val Thr Pro Ser Gly Ala Gly Glu Gln Asn
    370                 375                 380

Met Ile Gly Met Thr Pro Thr Val Ile Ala Val His Tyr Leu Asp Glu
385                 390                 395                 400

Thr Glu Gln Trp Glu Lys Phe Gly Leu Glu Lys Arg Gln Gly Ala Leu
                405                 410                 415
```

```
Glu Leu Ile Lys Lys Gly Tyr Thr Gln Gln Leu Ala Phe Arg Gln Pro
            420                 425                 430

Ser Ser Ala Phe Ala Ala Phe Val Lys Arg Ala Pro Ser Thr Trp Leu
        435                 440                 445

Thr Ala Tyr Val Val Lys Val Phe Ser Leu Ala Val Asn Leu Ile Ala
    450                 455                 460

Ile Asp Ser Gln Val Leu Cys Gly Ala Val Lys Trp Leu Ile Leu Glu
465                 470                 475                 480

Lys Gln Lys Pro Asp Gly Val Phe Gln Glu Asp Ala Pro Val Ile His
                485                 490                 495

Gln Glu Met Ile Gly Gly Leu Arg Asn Asn Asn Glu Lys Asp Met Ala
            500                 505                 510

Leu Thr Ala Phe Val Leu Ile Ser Leu Gln Glu Ala Lys Asp Ile Cys
        515                 520                 525

Glu Glu Gln Val Asn Ser Leu Pro Gly Ser Ile Thr Lys Ala Gly Asp
    530                 535                 540

Phe Leu Glu Ala Asn Tyr Met Asn Leu Gln Arg Ser Tyr Thr Val Ala
545                 550                 555                 560

Ile Ala Gly Tyr Ala Leu Ala Gln Met Gly Arg Leu Lys Gly Pro Leu
                565                 570                 575

Leu Asn Lys Phe Leu Thr Thr Ala Lys Asp Lys Asn Arg Trp Glu Asp
            580                 585                 590

Pro Gly Lys Gln Leu Tyr Asn Val Glu Ala Thr Ser Tyr Ala Leu Leu
        595                 600                 605

Ala Leu Leu Gln Leu Lys Asp Phe Asp Phe Val Pro Pro Val Val Arg
    610                 615                 620

Trp Leu Asn Glu Gln Arg Tyr Tyr Gly Gly Gly Tyr Gly Ser Thr Gln
625                 630                 635                 640

Ala Thr Phe Met Val Phe Gln Ala Leu Ala Gln Tyr Gln Lys Asp Ala
                645                 650                 655

Pro


<210> SEQ ID NO 8
<211> LENGTH: 618
<212> TYPE: PRT
<213> ORGANISM: Artificial Sequence
<220> FEATURE:
<223> OTHER INFORMATION: Synthesized

<400> SEQUENCE: 8

Met Glu Phe Gly Leu Ser Trp Val Phe Leu Val Ala Leu Leu Arg Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ala Val Ile Asp Ser Asn Gly Gly Ser Thr Tyr Tyr Pro
65                  70                  75                  80

Asp Thr Val Lys Asp Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ser Ser Tyr Thr Asn Leu Gly Ala Tyr Trp Gly Gln Gly
```

-continued

```
        115                 120                 125

Thr Leu Val Thr Val Ser Ala Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Ser Gly Tyr Leu Asn Trp Leu Gln Gln Lys Pro Gly Lys
            180                 185                 190

Ala Ile Lys Arg Leu Ile Tyr Thr Thr Ser Thr Leu Asp Ser Gly Val
        195                 200                 205

Pro Ser Arg Phe Ser Gly Ser Gly Ser Gly Thr Asp Phe Thr Leu Thr
    210                 215                 220

Ile Ser Ser Leu Gln Pro Glu Asp Phe Ala Thr Tyr Tyr Cys Leu Gln
225                 230                 235                 240

Tyr Ala Ser Ser Pro Phe Thr Phe Gly Gly Gly Thr Lys Val Glu Ile
                245                 250                 255

Lys Pro Ala Gly Gly Gly Gly Gly Ser Glu Val Gln Leu Val Glu Ser
            260                 265                 270

Gly Gly Gly Leu Val Gln Pro Gly Gly Ser Leu Arg Leu Ser Cys Ala
        275                 280                 285

Ala Ser Gly Tyr Ser Phe Thr Gly Tyr Thr Met Asn Trp Val Arg Gln
    290                 295                 300

Ala Pro Gly Lys Gly Leu Glu Trp Val Ala Leu Ile Asn Pro Tyr Lys
305                 310                 315                 320

Gly Val Ser Thr Tyr Asn Gln Lys Phe Lys Asp Arg Phe Thr Ile Ser
                325                 330                 335

Val Asp Lys Ser Lys Asn Thr Ala Tyr Leu Gln Met Asn Ser Leu Arg
            340                 345                 350

Ala Glu Asp Thr Ala Val Tyr Tyr Cys Ala Arg Ser Gly Tyr Tyr Gly
        355                 360                 365

Asp Ser Asp Trp Tyr Phe Asp Val Trp Gly Gln Gly Thr Leu Val Thr
    370                 375                 380

Val Ser Ser Gly Ala Pro Gly Gly Gly Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser Gln Glu Asp Pro Glu Val Gln Phe Asn Trp
        435                 440                 445

Tyr Val Asp Gly Val Glu Val His Asn Ala Lys Thr Lys Pro Arg Glu
    450                 455                 460

Glu Gln Phe Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Gly Leu Pro Ser Ser Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Trp Cys Leu Val Lys Gly Phe Tyr
    530                 535                 540
```

Pro Ser Asp Ile Ala Val Glu Trp Glu Ser Asn Gly Gln Pro Glu Asn
545 550 555 560

Asn Tyr Lys Thr Thr Pro Pro Val Leu Asp Ser Asp Gly Ser Phe Phe
565 570 575

Leu Tyr Ser Lys Leu Thr Val Asp Lys Ser Arg Trp Gln Gln Gly Asn
580 585 590

Val Phe Ser Cys Ser Val Met His Glu Ala Leu His Asn His Tyr Thr
595 600 605

Gln Lys Ser Leu Ser Leu Ser Pro Gly Lys
610 615

<210> SEQ ID NO 9
<211> LENGTH: 657
<212> TYPE: PRT
<213> ORGANISM: Artificial Sequence
<220> FEATURE:
<223> OTHER INFORMATION: Synthesized

<400> SEQUENCE: 9

Met Arg Leu Pro Ala Gln Leu Leu Gly Leu Leu Met Leu Trp Val Ser
1 5 10 15

Gly Ser Ser Gly Asp Ile Gln Met Thr Gln Ser Pro Ser Ser Leu Ser
20 25 30

Ala Ser Val Gly Asp Arg Val Thr Ile Thr Cys Arg Ala Ser Glu Asn
35 40 45

Ile Asp Asn Tyr Leu Ala Trp Tyr Gln Gln Lys Pro Gly Lys Val Pro
50 55 60

Lys Leu Leu Ile Tyr Ala Ala Thr Asn Leu Ala Asp Gly Val Pro Ser
65 70 75 80

Arg Phe Ser Gly Ser Gly Ser Gly Thr Asp Phe Thr Leu Thr Ile Ser
85 90 95

Ser Leu Gln Pro Glu Asp Val Ala Thr Tyr Tyr Cys Gln His Tyr Tyr
100 105 110

Ser Asn Gln Leu Thr Phe Gly Gln Gly Thr Lys Leu Glu Ile Lys Gly
115 120 125

Ala Pro Gly Gly Gly Thr His Thr Cys Pro Pro Cys Pro Ala Pro Glu
130 135 140

Leu Leu Gly Gly Pro Ser Val Phe Leu Phe Pro Pro Lys Pro Lys Asp
145 150 155 160

Thr Leu Met Ile Ser Arg Thr Pro Glu Val Thr Cys Val Val Val Asp
165 170 175

Val Ser Gln Glu Asp Pro Glu Val Gln Phe Asn Trp Tyr Val Asp Gly
180 185 190

Val Glu Val His Asn Ala Lys Thr Lys Pro Arg Glu Glu Gln Phe Asn
195 200 205

Ser Thr Tyr Arg Val Val Ser Val Leu Thr Val Leu His Gln Asp Trp
210 215 220

Leu Asn Gly Lys Glu Tyr Lys Cys Lys Val Ser Asn Lys Gly Leu Pro
225 230 235 240

Ser Ser Ile Glu Lys Thr Ile Ser Lys Ala Lys Gly Gln Pro Arg Glu
245 250 255

Pro Gln Val Tyr Thr Leu Pro Pro Ser Arg Glu Glu Met Thr Lys Asn
260 265 270

Gln Val Ser Leu Ser Cys Ala Val Lys Gly Phe Tyr Pro Ser Asp Ile
275 280 285

```
Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Val Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys Pro Ala Gly Gly Gly Gly Val Asp Ala Glu
        355                 360                 365

Arg Leu Lys His Leu Ile Val Thr Pro Ser Gly Ala Gly Glu Gln Asn
    370                 375                 380

Met Ile Gly Met Thr Pro Thr Val Ile Ala Val His Tyr Leu Asp Glu
385                 390                 395                 400

Thr Glu Gln Trp Glu Lys Phe Gly Leu Glu Lys Arg Gln Gly Ala Leu
                405                 410                 415

Glu Leu Ile Lys Lys Gly Tyr Thr Gln Gln Leu Ala Phe Arg Gln Pro
            420                 425                 430

Ser Ser Ala Phe Ala Ala Phe Val Lys Arg Ala Pro Ser Thr Trp Leu
        435                 440                 445

Thr Ala Tyr Val Val Lys Val Phe Ser Leu Ala Val Asn Leu Ile Ala
    450                 455                 460

Ile Asp Ser Gln Val Leu Cys Gly Ala Val Lys Trp Leu Ile Leu Glu
465                 470                 475                 480

Lys Gln Lys Pro Asp Gly Val Phe Gln Glu Asp Ala Pro Val Ile His
                485                 490                 495

Gln Glu Met Ile Gly Gly Leu Arg Asn Asn Asn Glu Lys Asp Met Ala
            500                 505                 510

Leu Thr Ala Phe Val Leu Ile Ser Leu Gln Glu Ala Lys Asp Ile Cys
        515                 520                 525

Glu Glu Gln Val Asn Ser Leu Pro Gly Ser Ile Thr Lys Ala Gly Asp
    530                 535                 540

Phe Leu Glu Ala Asn Tyr Met Asn Leu Gln Arg Ser Tyr Thr Val Ala
545                 550                 555                 560

Ile Ala Gly Tyr Ala Leu Ala Gln Met Gly Arg Leu Lys Gly Pro Leu
                565                 570                 575

Leu Asn Lys Phe Leu Thr Thr Ala Lys Asp Lys Asn Arg Trp Glu Asp
            580                 585                 590

Pro Gly Lys Gln Leu Tyr Asn Val Glu Ala Thr Ser Tyr Ala Leu Leu
        595                 600                 605

Ala Leu Leu Gln Leu Lys Asp Phe Asp Phe Val Pro Pro Val Val Arg
    610                 615                 620

Trp Leu Asn Glu Gln Arg Tyr Tyr Gly Gly Gly Tyr Gly Ser Thr Gln
625                 630                 635                 640

Ala Thr Phe Met Val Phe Gln Ala Leu Ala Gln Tyr Gln Lys Asp Ala
                645                 650                 655

Pro
```

<210> SEQ ID NO 10
<211> LENGTH: 669
<212> TYPE: PRT
<213> ORGANISM: Artificial Sequence
<220> FEATURE:
<223> OTHER INFORMATION: Synthesized

<400> SEQUENCE: 10

```
Met Glu Phe Gly Leu Ser Trp Val Phe Leu Val Ala Leu Leu Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Thr Met Ser Trp Val Arg Gln Ala Pro Gly Lys Gly Leu
    50                  55                  60

Glu Trp Val Ala Asn Ile Asn Ser Asp Gly Tyr Asn Ile Tyr Tyr Ser
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Cys Ser Tyr Tyr Ser Tyr Asp Tyr Phe Asp Tyr
        115                 120                 125

Trp Gly Gln Gly Thr Leu Val Thr Val Ser Ser Gly Ala Pro Gly Gly
    130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser Gln Glu
            180                 185                 190

Asp Pro Glu Val Gln Phe Asn Trp Tyr Val Asp Gly Val Glu Val His
        195                 200                 205

Asn Ala Lys Thr Lys Pro Arg Glu Glu Gln Phe Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Gly Leu Pro Ser Ser Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Trp Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys Pro Ala Gly Gly Gly Gly Val Asp Ala Glu Arg Leu Lys His
    370                 375                 380

Leu Ile Val Thr Pro Ser Gly Ala Gly Glu Gln Asn Met Ile Gly Met
385                 390                 395                 400

Thr Pro Thr Val Ile Ala Val His Tyr Leu Asp Glu Thr Glu Gln Trp
```

```
                405                 410                 415

Glu Lys Phe Gly Leu Glu Lys Arg Gln Gly Ala Leu Glu Leu Ile Lys
            420                 425                 430

Lys Gly Tyr Thr Gln Gln Leu Ala Phe Arg Gln Pro Ser Ser Ala Phe
        435                 440                 445

Ala Ala Phe Val Lys Arg Ala Pro Ser Thr Trp Leu Thr Ala Tyr Val
    450                 455                 460

Val Lys Val Phe Ser Leu Ala Val Asn Leu Ile Ala Ile Asp Ser Gln
465                 470                 475                 480

Val Leu Cys Gly Ala Val Lys Trp Leu Ile Leu Glu Lys Gln Lys Pro
            485                 490                 495

Asp Gly Val Phe Gln Glu Asp Ala Pro Val Ile His Gln Glu Met Ile
            500                 505                 510

Gly Gly Leu Arg Asn Asn Asn Glu Lys Asp Met Ala Leu Thr Ala Phe
        515                 520                 525

Val Leu Ile Ser Leu Gln Glu Ala Lys Asp Ile Cys Glu Glu Gln Val
    530                 535                 540

Asn Ser Leu Pro Gly Ser Ile Thr Lys Ala Gly Asp Phe Leu Glu Ala
545                 550                 555                 560

Asn Tyr Met Asn Leu Gln Arg Ser Tyr Thr Val Ala Ile Ala Gly Tyr
            565                 570                 575

Ala Leu Ala Gln Met Gly Arg Leu Lys Gly Pro Leu Leu Asn Lys Phe
            580                 585                 590

Leu Thr Thr Ala Lys Asp Lys Asn Arg Trp Glu Asp Pro Gly Lys Gln
        595                 600                 605

Leu Tyr Asn Val Glu Ala Thr Ser Tyr Ala Leu Leu Ala Leu Leu Gln
    610                 615                 620

Leu Lys Asp Phe Asp Phe Val Pro Pro Val Val Arg Trp Leu Asn Glu
625                 630                 635                 640

Gln Arg Tyr Tyr Gly Gly Gly Tyr Gly Ser Thr Gln Ala Thr Phe Met
                645                 650                 655

Val Phe Gln Ala Leu Ala Gln Tyr Gln Lys Asp Ala Pro
            660                 665


<210> SEQ ID NO 11
<211> LENGTH: 603
<212> TYPE: PRT
<213> ORGANISM: Artificial Sequence
<220> FEATURE:
<223> OTHER INFORMATION: Synthesized

<400> SEQUENCE: 11

Met Glu Phe Gly Leu Ser Trp Val Phe Leu Val Ala Leu Leu Arg Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ala Val Ile Asp Ser Asn Gly Gly Ser Thr Tyr Tyr Pro
65                  70                  75                  80

Asp Thr Val Lys Asp Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
```

```
            100                 105                 110

Tyr Tyr Cys Ser Ser Tyr Thr Asn Leu Gly Ala Tyr Trp Gly Gln Gly
        115                 120                 125

Thr Leu Val Thr Val Ser Ala Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Ser Gly Tyr Leu Asn Trp Leu Gln Gln Lys Pro Gly Lys
            180                 185                 190

Ala Ile Lys Arg Leu Ile Tyr Thr Thr Ser Thr Leu Asp Ser Gly Val
        195                 200                 205

Pro Ser Arg Phe Ser Gly Ser Gly Ser Gly Thr Asp Phe Thr Leu Thr
    210                 215                 220

Ile Ser Ser Leu Gln Pro Glu Asp Phe Ala Thr Tyr Tyr Cys Leu Gln
225                 230                 235                 240

Tyr Ala Ser Ser Pro Phe Thr Phe Gly Gly Gly Thr Lys Val Glu Ile
                245                 250                 255

Lys Pro Ala Gly Gly Gly Gly Gly Ser Asp Ile Gln Met Thr Gln Ser
            260                 265                 270

Pro Ser Ser Leu Ser Ala Ser Val Gly Asp Arg Val Thr Ile Thr Cys
        275                 280                 285

Gln Ala Ser Gln Asp Ile Ser Asn Tyr Leu Asn Trp Tyr Gln Gln Lys
    290                 295                 300

Pro Gly Lys Ala Pro Lys Leu Leu Ile Tyr Tyr Thr Ser Arg Leu Glu
305                 310                 315                 320

Ser Gly Val Pro Ser Arg Phe Ser Gly Ser Gly Ser Gly Thr Asp Tyr
                325                 330                 335

Thr Leu Thr Ile Ser Ser Leu Gln Pro Glu Asp Phe Ala Thr Tyr Tyr
            340                 345                 350

Cys Gln Gln Gly Asn Thr Leu Pro Trp Thr Phe Gly Gln Gly Thr Lys
        355                 360                 365

Val Glu Ile Lys Gly Ala Pro Gly Gly Gly Thr His Thr Cys Pro Pro
    370                 375                 380

Cys Pro Ala Pro Glu Leu Leu Gly Gly Pro Ser Val Phe Leu Phe Pro
385                 390                 395                 400

Pro Lys Pro Lys Asp Thr Leu Met Ile Ser Arg Thr Pro Glu Val Thr
                405                 410                 415

Cys Val Val Val Asp Val Ser Gln Glu Asp Pro Glu Val Gln Phe Asn
            420                 425                 430

Trp Tyr Val Asp Gly Val Glu Val His Asn Ala Lys Thr Lys Pro Arg
        435                 440                 445

Glu Glu Gln Phe Asn Ser Thr Tyr Arg Val Val Ser Val Leu Thr Val
    450                 455                 460

Leu His Gln Asp Trp Leu Asn Gly Lys Glu Tyr Lys Cys Lys Val Ser
465                 470                 475                 480

Asn Lys Gly Leu Pro Ser Ser Ile Glu Lys Thr Ile Ser Lys Ala Lys
                485                 490                 495

Gly Gln Pro Arg Glu Pro Gln Val Tyr Thr Leu Pro Pro Ser Arg Glu
            500                 505                 510

Glu Met Thr Lys Asn Gln Val Ser Leu Ser Cys Ala Val Lys Gly Phe
        515                 520                 525
```

```
Tyr Pro Ser Asp Ile Ala Val Glu Trp Glu Ser Asn Gly Gln Pro Glu
    530                 535                 540

Asn Asn Tyr Lys Thr Thr Pro Pro Val Leu Asp Ser Asp Gly Ser Phe
545                 550                 555                 560

Phe Leu Val Ser Lys Leu Thr Val Asp Lys Ser Arg Trp Gln Gln Gly
                565                 570                 575

Asn Val Phe Ser Cys Ser Val Met His Glu Ala Leu His Asn His Tyr
            580                 585                 590

Thr Gln Lys Ser Leu Ser Leu Ser Pro Gly Lys
        595                 600


<210> SEQ ID NO 12
<211> LENGTH: 608
<212> TYPE: PRT
<213> ORGANISM: Artificial Sequence
<220> FEATURE:
<223> OTHER INFORMATION: Synthesized

<400> SEQUENCE: 12

Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Asp Asn Tyr Leu Ala Trp Tyr Gln Gln Lys Pro Gly Lys Val Pro
    50                  55                  60

Lys Leu Leu Ile Tyr Ala Ala Thr Asn Leu Ala Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln His Tyr Tyr
            100                 105                 110

Ser Asn Gln Leu Thr Phe Gly Gln Gly Thr Lys Leu Glu Ile Lys Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Phe Thr Phe Ser Thr Tyr Thr Met
                165                 170                 175

Ser Trp Val Arg Gln Ala Pro Gly Lys Gly Leu Glu Trp Val Ala Asn
            180                 185                 190

Ile Asn Ser Asp Gly Tyr Asn Ile Tyr Tyr Ser Asp Ser Val Lys Gly
        195                 200                 205

Arg Phe Thr Ile Ser Arg Asp Asn Ala Lys Asn Ser Leu Tyr Leu Gln
    210                 215                 220

Met Asn Ser Leu Arg Ala Glu Asp Thr Ala Val Tyr Tyr Cys Val Arg
225                 230                 235                 240

Cys Ser Tyr Tyr Ser Tyr Asp Tyr Phe Asp Tyr Trp Gly Gln Gly Thr
                245                 250                 255

Leu Val Thr Val Ser Ser Pro Ala Gly Gly Gly Gly Ser Asp Ile
            260                 265                 270

Gln Met Thr Gln Ser Pro Ser Ser Leu Ser Ala Ser Val Gly Asp Arg
        275                 280                 285
```

```
Val Thr Ile Thr Cys Gln Ala Ser Gln Asp Ile Ser Asn Tyr Leu Asn
    290                 295                 300

Trp Tyr Gln Gln Lys Pro Gly Lys Ala Pro Lys Leu Leu Ile Tyr Tyr
305                 310                 315                 320

Thr Ser Arg Leu Glu Ser Gly Val Pro Ser Arg Phe Ser Gly Ser Gly
                325                 330                 335

Ser Gly Thr Asp Tyr Thr Leu Thr Ile Ser Ser Leu Gln Pro Glu Asp
            340                 345                 350

Phe Ala Thr Tyr Tyr Cys Gln Gln Gly Asn Thr Leu Pro Trp Thr Phe
        355                 360                 365

Gly Gln Gly Thr Lys Val Glu Ile Lys Gly Ala Pro Gly Gly Gly Thr
    370                 375                 380

His Thr Cys Pro Pro Cys Pro Ala Pro Glu Leu Leu Gly Gly Pro Ser
385                 390                 395                 400

Val Phe Leu Phe Pro Pro Lys Pro Lys Asp Thr Leu Met Ile Ser Arg
                405                 410                 415

Thr Pro Glu Val Thr Cys Val Val Val Asp Val Ser Gln Glu Asp Pro
            420                 425                 430

Glu Val Gln Phe Asn Trp Tyr Val Asp Gly Val Glu Val His Asn Ala
        435                 440                 445

Lys Thr Lys Pro Arg Glu Glu Gln Phe Asn Ser Thr Tyr Arg Val Val
    450                 455                 460

Ser Val Leu Thr Val Leu His Gln Asp Trp Leu Asn Gly Lys Glu Tyr
465                 470                 475                 480

Lys Cys Lys Val Ser Asn Lys Gly Leu Pro Ser Ser Ile Glu Lys Thr
                485                 490                 495

Ile Ser Lys Ala Lys Gly Gln Pro Arg Glu Pro Gln Val Tyr Thr Leu
            500                 505                 510

Pro Pro Ser Arg Glu Glu Met Thr Lys Asn Gln Val Ser Leu Ser Cys
        515                 520                 525

Ala Val Lys Gly Phe Tyr Pro Ser Asp Ile Ala Val Glu Trp Glu Ser
    530                 535                 540

Asn Gly Gln Pro Glu Asn Asn Tyr Lys Thr Thr Pro Pro Val Leu Asp
545                 550                 555                 560

Ser Asp Gly Ser Phe Phe Leu Val Ser Lys Leu Thr Val Asp Lys Ser
                565                 570                 575

Arg Trp Gln Gln Gly Asn Val Phe Ser Cys Ser Val Met His Glu Ala
            580                 585                 590

Leu His Asn His Tyr Thr Gln Lys Ser Leu Ser Leu Ser Pro Gly Lys
        595                 600                 605


<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105


<210> SEQ ID NO 14
<211> LENGTH: 866
<212> TYPE: PRT
<213> ORGANISM: Artificial Sequence
<220> FEATURE:
<223> OTHER INFORMATION: Synthesized

<400> SEQUENCE: 14

Met Arg Leu Pro Ala Gln Leu Leu Gly Leu Leu Met Leu Trp Val Ser
1               5                   10                  15

Gly Ser Ser Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Asp Asn Tyr Leu Ala Trp Tyr Gln Gln Lys Pro Gly Lys Val Pro
    50                  55                  60

Lys Leu Leu Ile Tyr Ala Ala Thr Asn Leu Ala Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln His Tyr Tyr
            100                 105                 110

Ser Asn Gln Leu Thr Phe Gly Gln Gly Thr Lys Leu Glu Ile Lys Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Phe Thr Phe Ser Thr Tyr Thr Met
                165                 170                 175

Ser Trp Val Arg Gln Ala Pro Gly Lys Gly Leu Glu Trp Val Ala Asn
            180                 185                 190

Ile Asn Ser Asp Gly Tyr Asn Ile Tyr Tyr Ser Asp Ser Val Lys Gly
        195                 200                 205

Arg Phe Thr Ile Ser Arg Asp Asn Ala Lys Asn Ser Leu Tyr Leu Gln
    210                 215                 220

Met Asn Ser Leu Arg Ala Glu Asp Thr Ala Val Tyr Tyr Cys Val Arg
225                 230                 235                 240

Cys Ser Tyr Tyr Ser Tyr Asp Tyr Phe Asp Tyr Trp Gly Gln Gly Thr
                245                 250                 255

Leu Val Thr Val Ser Ser Pro Ala Gly Gly Gly Gly Gly Ser Asp Ile
            260                 265                 270

Gln Met Thr Gln Ser Pro Ser Ser Leu Ser Ala Ser Val Gly Asp Arg
        275                 280                 285

Val Thr Ile Thr Cys Gln Ala Ser Gln Asp Ile Ser Asn Tyr Leu Asn
    290                 295                 300
```

```
Trp Tyr Gln Gln Lys Pro Gly Lys Ala Pro Lys Leu Leu Ile Tyr Tyr
305                 310                 315                 320

Thr Ser Arg Leu Glu Ser Gly Val Pro Ser Arg Phe Ser Gly Ser Gly
                325                 330                 335

Ser Gly Thr Asp Tyr Thr Leu Thr Ile Ser Ser Leu Gln Pro Glu Asp
            340                 345                 350

Phe Ala Thr Tyr Tyr Cys Gln Gln Gly Asn Thr Leu Pro Trp Thr Phe
        355                 360                 365

Gly Gln Gly Thr Lys Val Glu Ile Lys Gly Ala Pro Gly Gly Gly Thr
    370                 375                 380

His Thr Cys Pro Pro Cys Pro Ala Pro Glu Leu Leu Gly Gly Pro Ser
385                 390                 395                 400

Val Phe Leu Phe Pro Pro Lys Pro Lys Asp Thr Leu Met Ile Ser Arg
                405                 410                 415

Thr Pro Glu Val Thr Cys Val Val Val Asp Val Ser Gln Glu Asp Pro
            420                 425                 430

Glu Val Gln Phe Asn Trp Tyr Val Asp Gly Val Glu Val His Asn Ala
        435                 440                 445

Lys Thr Lys Pro Arg Glu Glu Gln Phe Asn Ser Thr Tyr Arg Val Val
    450                 455                 460

Ser Val Leu Thr Val Leu His Gln Asp Trp Leu Asn Gly Lys Glu Tyr
465                 470                 475                 480

Lys Cys Lys Val Ser Asn Lys Gly Leu Pro Ser Ser Ile Glu Lys Thr
                485                 490                 495

Ile Ser Lys Ala Lys Gly Gln Pro Arg Glu Pro Gln Val Tyr Thr Leu
            500                 505                 510

Pro Pro Ser Arg Glu Glu Met Thr Lys Asn Gln Val Ser Leu Ser Cys
        515                 520                 525

Ala Val Lys Gly Phe Tyr Pro Ser Asp Ile Ala Val Glu Trp Glu Ser
    530                 535                 540

Asn Gly Gln Pro Glu Asn Asn Tyr Lys Thr Thr Pro Pro Val Leu Asp
545                 550                 555                 560

Ser Asp Gly Ser Phe Phe Leu Val Ser Lys Leu Thr Val Asp Lys Ser
                565                 570                 575

Arg Trp Gln Gln Gly Asn Val Phe Ser Cys Ser Val Met His Glu Ala
            580                 585                 590

Leu His Asn His Tyr Thr Gln Lys Ser Leu Ser Leu Ser Pro Gly Lys
        595                 600                 605

Pro Gly Gly Gly Gly Ser Gln Val Gln Leu Val Gln Ser Gly Ala Glu
    610                 615                 620

Val Lys Lys Pro Gly Ala Ser Val Lys Val Ser Cys Lys Ala Ser Gly
625                 630                 635                 640

Tyr Ser Phe Thr Asp Tyr Thr Met Asn Trp Val Arg Gln Ala Pro Gly
                645                 650                 655

Gln Gly Leu Glu Trp Met Gly Val Ile Asn Pro Asn His Gly Ile Ser
            660                 665                 670

Ser Tyr Ala Gln Lys Phe Gln Gly Arg Val Thr Met Thr Arg Asp Thr
        675                 680                 685

Ser Thr Ser Thr Val Tyr Met Glu Leu Ser Ser Leu Arg Ser Glu Asp
    690                 695                 700

Thr Ala Val Tyr Tyr Cys Val Arg Arg Lys Ile Ser Tyr Asp Tyr Asp
705                 710                 715                 720
```

Glu Gly Tyr Ala Met Asp Tyr Trp Gly Gln Gly Thr Leu Val Thr Val
725 730 735

Ser Ser Gly Gly Gly Gly Ser Gly Gly Gly Gly Ser Gly Gly Gly Gly
740 745 750

Ser Asp Ile Val Met Thr Gln Ser Pro Asp Ser Leu Ala Val Ser Leu
755 760 765

Gly Glu Arg Ala Thr Ile Asn Cys Lys Ser Ser Gln Asn Leu Leu Asn
770 775 780

Ser Ser Asn Gln Lys Asn Tyr Leu Ala Trp Tyr Gln Gln Lys Pro Gly
785 790 795 800

Gln Pro Pro Lys Leu Leu Val Phe Phe Ala Ala Thr Arg Glu Ser Gly
805 810 815

Val Pro Asp Arg Phe Ser Gly Ser Gly Ser Gly Thr Asp Phe Thr Leu
820 825 830

Thr Ile Ser Ser Leu Gln Ala Glu Asp Val Ala Val Tyr Tyr Cys Gln
835 840 845

Gln His Tyr Ser Thr Pro Trp Thr Phe Gly Gly Gly Thr Lys Leu Glu
850 855 860

Ile Lys
865

<210> SEQ ID NO 15
<211> LENGTH: 618
<212> TYPE: PRT
<213> ORGANISM: Artificial Sequence
<220> FEATURE:
<223> OTHER INFORMATION: Synthesized

<400> SEQUENCE: 15

Met Glu Phe Gly Leu Ser Trp Val Phe Leu Val Ala Leu Leu Arg Gly
1 5 10 15

Val Gln Cys Glu Val Gln Leu Leu Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Ala Met Ser Trp Val Arg Gln Ala Pro Gly Lys Gly Leu
50 55 60

Glu Trp Val Ala Val Ile Asp Ser Asn Gly Gly Ser Thr Tyr Tyr Pro
65 70 75 80

Asp Thr Val Lys Asp Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ser Ser Tyr Thr Asn Leu Gly Ala Tyr Trp Gly Gln Gly
115 120 125

Thr Leu Val Thr Val Ser Ala Gly Gly Gly Gly Ser Gly Gly Gly Gly
130 135 140

Ser Gly Gly Gly Gly Ser Asp Ile Gln Met Thr Gln Ser Pro Ser Ser
145 150 155 160

Leu Ser Ala Ser Val Gly Asp Arg Val Thr Ile Thr Cys Arg Ala Ser
165 170 175

Gln Asp Ile Ser Gly Tyr Leu Asn Trp Leu Gln Gln Lys Pro Gly Lys
180 185 190

Ala Ile Lys Arg Leu Ile Tyr Thr Thr Ser Thr Leu Asp Ser Gly Val
195 200 205

```
Pro Ser Arg Phe Ser Gly Ser Gly Ser Gly Thr Asp Phe Thr Leu Thr
    210                 215                 220

Ile Ser Ser Leu Gln Pro Glu Asp Phe Ala Thr Tyr Tyr Cys Leu Gln
225                 230                 235                 240

Tyr Ala Ser Ser Pro Phe Thr Phe Gly Gly Gly Thr Lys Val Glu Ile
                245                 250                 255

Lys Pro Ala Gly Gly Gly Gly Gly Ser Glu Val Gln Leu Val Glu Ser
            260                 265                 270

Gly Gly Gly Leu Val Gln Pro Gly Gly Ser Leu Arg Leu Ser Cys Ala
        275                 280                 285

Ala Ser Gly Tyr Ser Phe Thr Gly Tyr Thr Met Asn Trp Val Arg Gln
    290                 295                 300

Ala Pro Gly Lys Gly Leu Glu Trp Val Ala Leu Ile Asn Pro Tyr Lys
305                 310                 315                 320

Gly Val Ser Thr Tyr Asn Gln Lys Phe Lys Asp Arg Phe Thr Ile Ser
                325                 330                 335

Val Asp Lys Ser Lys Asn Thr Ala Tyr Leu Gln Met Asn Ser Leu Arg
            340                 345                 350

Ala Glu Asp Thr Ala Val Tyr Tyr Cys Ala Arg Ser Gly Tyr Tyr Gly
        355                 360                 365

Asp Ser Asp Trp Tyr Phe Asp Val Trp Gly Gln Gly Thr Leu Val Thr
    370                 375                 380

Val Ser Ser Gly Ala Pro Gly Gly Gly Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser Gln Glu Asp Pro Glu Val Gln Phe Asn Trp
        435                 440                 445

Tyr Val Asp Gly Val Glu Val His Asn Ala Lys Thr Lys Pro Arg Glu
    450                 455                 460

Glu Gln Phe Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Gly Leu Pro Ser Ser Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Trp Cys Leu Val Lys Gly Phe Tyr
    530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys
    610                 615
```

<210> SEQ ID NO 16
<211> LENGTH: 867
<212> TYPE: PRT
<213> ORGANISM: Artificial Sequence
<220> FEATURE:
<223> OTHER INFORMATION: Synthesized

<400> SEQUENCE: 16

```
Met Glu Phe Gly Leu Ser Trp Val Phe Leu Val Ala Leu Leu Arg Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ala Val Ile Asp Ser Asn Gly Gly Ser Thr Tyr Tyr Pro
65                  70                  75                  80

Asp Thr Val Lys Asp Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ser Ser Tyr Thr Asn Leu Gly Ala Tyr Trp Gly Gln Gly
        115                 120                 125

Thr Leu Val Thr Val Ser Ala Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Ser Gly Tyr Leu Asn Trp Leu Gln Gln Lys Pro Gly Lys
            180                 185                 190

Ala Ile Lys Arg Leu Ile Tyr Thr Thr Ser Thr Leu Asp Ser Gly Val
        195                 200                 205

Pro Ser Arg Phe Ser Gly Ser Gly Ser Gly Thr Asp Phe Thr Leu Thr
    210                 215                 220

Ile Ser Ser Leu Gln Pro Glu Asp Phe Ala Thr Tyr Tyr Cys Leu Gln
225                 230                 235                 240

Tyr Ala Ser Ser Pro Phe Thr Phe Gly Gly Gly Thr Lys Val Glu Ile
                245                 250                 255

Lys Pro Ala Gly Gly Gly Gly Gly Ser Glu Val Gln Leu Val Glu Ser
            260                 265                 270

Gly Gly Gly Leu Val Gln Pro Gly Gly Ser Leu Arg Leu Ser Cys Ala
        275                 280                 285

Ala Ser Gly Tyr Ser Phe Thr Gly Tyr Thr Met Asn Trp Val Arg Gln
    290                 295                 300

Ala Pro Gly Lys Gly Leu Glu Trp Val Ala Leu Ile Asn Pro Tyr Lys
305                 310                 315                 320

Gly Val Ser Thr Tyr Asn Gln Lys Phe Lys Asp Arg Phe Thr Ile Ser
                325                 330                 335

Val Asp Lys Ser Lys Asn Thr Ala Tyr Leu Gln Met Asn Ser Leu Arg
            340                 345                 350

Ala Glu Asp Thr Ala Val Tyr Tyr Cys Ala Arg Ser Gly Tyr Tyr Gly
        355                 360                 365

Asp Ser Asp Trp Tyr Phe Asp Val Trp Gly Gln Gly Thr Leu Val Thr
```

```
    370                 375                 380

Val Ser Ser Gly Ala Pro Gly Gly Gly Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser Gln Glu Asp Pro Glu Val Gln Phe Asn Trp
        435                 440                 445

Tyr Val Asp Gly Val Glu Val His Asn Ala Lys Thr Lys Pro Arg Glu
    450                 455                 460

Glu Gln Phe Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Gly Leu Pro Ser Ser Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Trp Cys Leu Val Lys Gly Phe Tyr
    530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys Pro Gly Gly Gly Gly Ser
    610                 615                 620

Glu Val Gln Leu Val Gln Ser Gly Gly Gly Val Glu Arg Pro Gly Gly
625                 630                 635                 640

Ser Leu Arg Leu Ser Cys Ala Ala Ser Gly Phe Thr Phe Asp Asp Tyr
                645                 650                 655

Gly Met Ser Trp Val Arg Gln Ala Pro Gly Lys Gly Leu Glu Trp Val
            660                 665                 670

Ser Gly Ile Asn Trp Asn Gly Gly Ser Thr Gly Tyr Ala Asp Ser Val
        675                 680                 685

Lys Gly Arg Val Thr Ile Ser Arg Asp Asn Ala Lys Asn Ser Leu Tyr
    690                 695                 700

Leu Gln Met Asn Ser Leu Arg Ala Glu Asp Thr Ala Val Tyr Tyr Cys
705                 710                 715                 720

Ala Lys Ile Leu Gly Ala Gly Arg Gly Trp Tyr Phe Asp Leu Trp Gly
                725                 730                 735

Lys Gly Thr Thr Val Thr Val Ser Gly Gly Gly Gly Ser Gly Gly Gly
            740                 745                 750

Gly Ser Gly Gly Gly Gly Ser Ser Ser Glu Leu Thr Gln Asp Pro Ala
        755                 760                 765

Val Ser Val Ala Leu Gly Gln Thr Val Arg Ile Thr Cys Gln Gly Asp
    770                 775                 780

Ser Leu Arg Ser Tyr Tyr Ala Ser Trp Tyr Gln Gln Lys Pro Gly Gln
785                 790                 795                 800
```

Ala Pro Val Leu Val Ile Tyr Gly Lys Asn Asn Arg Pro Ser Gly Ile
805 810 815

Pro Asp Arg Phe Ser Gly Ser Ser Ser Gly Asn Thr Ala Ser Leu Thr
820 825 830

Ile Thr Gly Ala Gln Ala Glu Asp Glu Ala Asp Tyr Tyr Cys Asn Ser
835 840 845

Arg Asp Ser Ser Gly Asn His Val Val Phe Gly Gly Gly Thr Lys Leu
850 855 860

Thr Val Leu
865

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Arg Ala Ser Gln Asp Ile Arg Asn Tyr
1 5

<210> SEQ ID NO 18
<211> LENGTH: 7
<212> TYPE: PRT
<213> ORGANISM: Artificial Sequence
<220> FEATURE:
<223> OTHER INFORMATION: Synthesized

<400> SEQUENCE: 18

Pro Ala Gly Gly Gly Gly Ser
1 5

<210> SEQ ID NO 19
<211> LENGTH: 6
<212> TYPE: PRT
<213> ORGANISM: Artificial Sequence
<220> FEATURE:
<223> OTHER INFORMATION: Synthesized

<400> SEQUENCE: 19

Pro Ala Gly Pro Pro Ala
1 5

<210> SEQ ID NO 20
<211> LENGTH: 6
<212> TYPE: PRT
<213> ORGANISM: Artificial Sequence
<220> FEATURE:
<223> OTHER INFORMATION: Synthesized

<400> SEQUENCE: 20

Pro Ala Gly Pro Ala Pro
1 5

<210> SEQ ID NO 21
<211> LENGTH: 6
<212> TYPE: PRT
<213> ORGANISM: Artificial Sequence
<220> FEATURE:
<223> OTHER INFORMATION: Synthesized

<400> SEQUENCE: 21

Pro Ala Gly Pro Pro Pro

-continued 1 5

<210> SEQ ID NO 22
<211> LENGTH: 7
<212> TYPE: PRT
<213> ORGANISM: Artificial Sequence
<220> FEATURE:
<223> OTHER INFORMATION: Synthesized

<400> SEQUENCE: 22

Gly Ala Pro Gly Gly Gly Gly
1 5